US012624390B2

(12) United States Patent
Malyshev et al.

(10) Patent No.: US 12,624,390 B2
(45) Date of Patent: *May 12, 2026

(54) DISTINGUISHING SEQUENCES BY DETECTING POLYMERASE DISSOCIATION

(71) Applicant: Pacific Biosciences of California, Inc., Menlo Park, CA (US)

(72) Inventors: Denis Malyshev, San Diego, CA (US); Sean Stromberg, San Diego, CA (US)

(73) Assignee: PACIFIC BIOSCIENCES OF CALIFORNIA, INC., Menlo Park, CA (US)

( * ) Notice: Subject to any disclaimer, the term of this patent is extended or adjusted under 35 U.S.C. 154(b) by 684 days.

This patent is subject to a terminal disclaimer.

(21) Appl. No.: 17/953,719

(22) Filed: Sep. 27, 2022

(65) Prior Publication Data

US 2023/0227900 A1     Jul. 20, 2023

Related U.S. Application Data

(63) Continuation of application No. 16/486,062, filed as application No. PCT/US2018/018118 on Feb. 14, 2018, now Pat. No. 11,492,666.

(60) Provisional application No. 62/459,437, filed on Feb. 15, 2017.

(51) Int. Cl.
*C12Q 1/6869*     (2018.01)

(52) U.S. Cl.
CPC ................................. *C12Q 1/6869* (2013.01)

(58) Field of Classification Search
CPC ..................................................... C12Q 1/6869
See application file for complete search history.

(56) References Cited

U.S. PATENT DOCUMENTS

| | | | |
|---|---|---|---|
| 5,302,509 A | 4/1994 | Cheeseman |
| 5,614,365 A | 3/1997 | Tabor et al. |
| 6,485,909 B1 | 11/2002 | Hong et al. |
| 6,720,177 B2 | 4/2004 | Ghadiri et al. |
| 6,828,094 B2 | 12/2004 | Kilger et al. |
| 6,908,736 B1 | 6/2005 | Densham |
| 7,008,766 B1 | 3/2006 | Densham |
| 7,223,540 B2 | 5/2007 | Pourmand et al. |
| 7,264,934 B2 | 9/2007 | Fuller |
| 7,329,492 B2 | 2/2008 | Hardin et al. |
| 7,449,297 B2 | 11/2008 | Freije et al. |
| 7,482,120 B2 | 1/2009 | Buzby |
| 7,604,963 B2 | 10/2009 | Densham |
| 7,635,578 B2 | 12/2009 | Ju et al. |

| | | | |
|---|---|---|---|
| 7,713,698 B2 | 5/2010 | Ju et al. |
| 7,790,869 B2 | 9/2010 | Ju et al. |
| 7,871,771 B2 | 1/2011 | Fuller et al. |
| 7,939,264 B1 | 5/2011 | Densham |
| 8,071,755 B2 | 12/2011 | Efcavitch et al. |
| 8,088,575 B2 | 1/2012 | Ju et al. |
| 8,133,672 B2 | 3/2012 | Bjornson et al. |
| 8,236,532 B2 | 8/2012 | Ronaghi et al. |
| 8,298,792 B2 | 10/2012 | Ju et al. |
| 8,399,196 B2 | 3/2013 | Hoser |
| 8,481,266 B2 | 7/2013 | Shao et al. |
| 8,535,881 B2 | 9/2013 | Schneider |
| 8,603,741 B2 | 12/2013 | Emig et al. |
| 8,632,975 B2 | 1/2014 | Vander Horn et al. |
| 8,658,365 B2 | 2/2014 | Bjornson et al. |
| 8,703,461 B2 | 4/2014 | Peris et al. |
| 8,911,972 B2 | 12/2014 | Chaisson et al. |
| 8,986,930 B2 | 3/2015 | Fedorov et al. |
| 9,255,258 B2 | 2/2016 | Vander Horn et al. |
| 9,279,154 B2 | 3/2016 | Previte et al. |
| 9,279,155 B2 | 3/2016 | Bjornson et al. |
| 9,476,094 B2 | 10/2016 | Densham |
| 9,951,385 B1 | 4/2018 | Vijayan et al. |
| 10,077,470 B2 | 9/2018 | Vijayan et al. |
| 10,246,744 B2 | 4/2019 | Vijayan et al. |
| 10,443,098 B2 | 10/2019 | Vijayan et al. |

(Continued)

FOREIGN PATENT DOCUMENTS

| | | |
|---|---|---|
| CN | 1537172 A | 10/2004 |
| CN | 1553953 A | 12/2004 |

(Continued)

OTHER PUBLICATIONS

Metzker, Michael L. "Sequencing technologies—the next generation." Nature reviews genetics 11.1 (2010): 31-46. (Year: 2010).*

(Continued)

*Primary Examiner* — Robert J Yamasaki

(74) *Attorney, Agent, or Firm* — Kilpatrick Townsend & Stockton LLP

(57)     ABSTRACT

A method for determining the presence of an allele, including (a) binding a polymerase to a double stranded nucleic acid that includes a primer hybridized to a template, the template including a first allele of a locus; (b) adding a nucleotide to the primer via catalytic activity of the polymerase, thereby producing an extended nucleic acid; (c) dissociating the polymerase from the extended nucleic acid; (d) detecting dissociation of the polymerase from the extended nucleic acid; and (e) comparing the dissociation of the polymerase from the extended nucleic acid to dissociation of the polymerase from a second double stranded nucleic acid, the second double stranded nucleic acid including a primer hybridized to the same position of the locus as the primer of the extended nucleic acid.

1 Claim, 2 Drawing Sheets

Specification includes a Sequence Listing.

(56) References Cited

U.S. PATENT DOCUMENTS

| | | | |
|---|---|---|---|
| 10,982,264 | B2 | 4/2021 | Dambacher |
| 11,492,666 | B2 | 11/2022 | Malyshev et al. |
| 11,499,185 | B2 | 11/2022 | Vijayan et al. |
| 2006/0051807 | A1 | 3/2006 | Fuller |
| 2006/0292583 | A1 | 12/2006 | Schneider et al. |
| 2007/0009925 | A1 | 1/2007 | Fang et al. |
| 2009/0061447 | A1 | 3/2009 | Schneider |
| 2010/0311061 | A1 | 12/2010 | Korlach et al. |
| 2010/0316999 | A1 | 12/2010 | Densham |
| 2010/0317012 | A1 | 12/2010 | Ju et al. |
| 2010/0330570 | A1 | 12/2010 | Vander Horn et al. |
| 2011/0008794 | A1 | 1/2011 | Schneider |
| 2011/0160077 | A1 | 6/2011 | Chaisson et al. |
| 2011/0237464 | A1 | 9/2011 | Cunningham et al. |
| 2011/0262922 | A1 | 10/2011 | Chae et al. |
| 2013/0165328 | A1 | 6/2013 | Previte et al. |
| 2013/0316642 | A1 | 11/2013 | Newham |
| 2014/0127680 | A1 | 5/2014 | Emig et al. |
| 2014/0234940 | A1 | 8/2014 | Peris et al. |
| 2016/0010150 | A1 | 1/2016 | Emig et al. |
| 2016/0098518 | A1 | 4/2016 | Royce et al. |
| 2016/0168633 | A1 | 6/2016 | Previte et al. |
| 2016/0177384 | A1 | 6/2016 | Bjornson et al. |
| 2016/0208318 | A1 | 7/2016 | Vander Horn et al. |
| 2017/0022553 | A1 | 1/2017 | Vijayan et al. |

FOREIGN PATENT DOCUMENTS

| | | |
|---|---|---|
| CN | 107849605 A | 3/2018 |
| EP | 1115848 A1 | 7/2001 |
| EP | 3325642 B1 | 5/2018 |
| JP | 2004513619 A | 5/2004 |
| JP | 2006308292 A | 11/2006 |
| JP | 2008502369 A | 1/2008 |
| JP | 2008104463 A | 5/2008 |
| JP | 2011525810 A | 9/2011 |
| JP | 2018527020 A | 9/2018 |
| WO | 1990013666 A1 | 11/1990 |
| WO | 0116375 A2 | 3/2001 |
| WO | 0204680 A2 | 1/2002 |
| WO | 02068684 A2 | 9/2002 |
| WO | 2005121363 A2 | 12/2005 |
| WO | 2005123957 A2 | 12/2005 |
| WO | 2009145820 A2 | 12/2009 |
| WO | 2009145828 A2 | 12/2009 |
| WO | 2010008480 A2 | 1/2010 |
| WO | 2010068884 A2 | 6/2010 |
| WO | 2010111690 A2 | 9/2010 |
| WO | 2010141390 A2 | 12/2010 |
| WO | 2011159942 A1 | 12/2011 |
| WO | 2012166742 A3 | 12/2012 |
| WO | 2013096692 A1 | 6/2013 |
| WO | 2017014762 A1 | 1/2017 |
| WO | 2017184996 A1 | 10/2017 |
| WO | 2018034780 A1 | 2/2018 |

OTHER PUBLICATIONS

U.S. Appl. No. 16/486,062, "Final Office Action", Feb. 28, 2022, 10 pages.

U.S. Appl. No. 16/486,062, "Non-Final Office Action", Jul. 7, 2021, 29 pages.

PCT/US2018/018118, "International Preliminary Report on Patentability", Aug. 29, 2019, 7 pages.

PCT/US2018/018118, "International Search Report and Written Opinion", May 23, 2018, 12 pages.

"APCH231: Chemical Analysis Complexometric Titrations EDTA", Notes Compiled by Dr. C. Southway, Available Online at: http://cheminnerweb.ukzn.ac.za/libraries/apch231_h_govender_s_notes/apch231_edta.sflb.ashx, Nov. 23, 2015, pp. 30-42.

"Ion Torrent Amplicon Sequencing", Application Note Amplicon Sequencing, Available Online at: http://www.iontorrent.com/lib/ images/PDFs/amplicon_application_note_040411.pdf, XP-002681382, Apr. 4, 2011, 5 pages.

U.S. Appl. No. 14/805,381, "Final Office Action", Dec. 14, 2017, 17 pages.

U.S. Appl. No. 14/805,381, "Non-Final Office Action", Aug. 24, 2017, 13 pages.

U.S. Appl. No. 14/805,381, "Non-Final Office Action", Feb. 12, 2018, 20 pages.

U.S. Appl. No. 14/805,381, "Notice of Allowance", Jul. 3, 2018, 10 pages.

U.S. Appl. No. 16/046,707, "Final Office Action", Oct. 1, 2021, 16 pages.

U.S. Appl. No. 16/046,707, "Non-Final Office Action", Aug. 21, 2020, 15 pages.

U.S. Appl. No. 16/046,707, "Non-Final Office Action", Feb. 17, 2022, 9 pages.

U.S. Appl. No. 16/046,707, "Notice of Allowance", Jul. 13, 2022, 8 pages.

U.S. Appl. No. 16/078,261, "Non-Final Office Action", Aug. 6, 2020, 13 pages.

U.S. Appl. No. 16/078,261, "Notice of Allowance", Feb. 3, 2021, 12 pages.

Agnarsson et al., "On-Chip Modulation of Evanescent Illumination and Live-Cell Imaging with Polymer Waveguides", Optics Express, vol. 19, No. 23, Nov. 7, 2011, pp. 22929-22935.

Anker et al., "Biosensing with Plasmonic Nanosensors", Nature Materials, vol. 7, No. 6, Jun. 2008, pp. 442-453.

AU2015402762, "First Examination Report", Sep. 9, 2019, 3 pages.

AU2017254688, "First Examination Report", Nov. 21, 2019, 4 pages.

AU2017254688, "Second Examination Report", Feb. 17, 2020, 3 pages.

Bandwar et al., "Peculiar 2-Aminopurine Fluorescence Monitors the Dynamics of Open Complex Formation by Bacteriophage T7 RNA Polymerase", The Journal of Biological Chemistry, vol. 276, No. 17, Apr. 27, 2001, pp. 14075-14082.

Brockman et al., "A Multistep Chemical Modification Procedure to Create DNA Arrays on Gold Surfaces for the Study of Protein—DNA Interactions with Surface Plasmon Resonance Imaging", Journal of the American Chemical Society, vol. 121, No. 35, Aug. 19, 1999, pp. 8044-8051.

Brown et al., "Pre-Steady-State Kinetic Analysis of Truncated and Full-Length *Saccharomyces cerevisiae* DNA Polymerase Eta", Journal of Nucleic Acids, vol. 2010, Article ID 871939, Jul. 25, 2010, 12 pages.

CA2,992,980, "Office Action", Apr. 6, 2021, 4 pages.

CA2,992,980, "Office Action", Mar. 3, 2022, 4 pages.

CA2,992,980, "Office Action", Mar. 6, 2023, 4 pages.

CA3,011,635, "Notice of Allowance", Jun. 18, 2021, 1 page.

CA3,011,635, "Office Action", Jun. 11, 2020, 4 pages.

CA3,011,635, "Office Action", Jun. 4, 2019, 4 pages.

Campagnola et al., "High-Throughput Screening Identification of Poliovirus RNA-Dependent RNA Polymerase Inhibitors", Antiviral Research, vol. 91, No. 3, Sep. 2011, 21 pages.

Chan et al., "A General Method for Discovering Inhibitors of Protein-DNA Interactions Using Photonic Crystal Biosensors", ACS Chemical Biology, vol. 3, No. 7, Jul. 18, 2008, 18 pages.

Chen et al., "The History and Advances of Reversible Terminators Used in New Generations of Sequencing Technology", Genomics Proteomics Bioinformatics, vol. 11, No. 1, Feb. 1, 2013, pp. 34-40.

Chin et al., "The Effect of Divalent Nickel (Ni2+) on in Vivo DNA Replication by DNA Polymerase α1", Cancer Research, vol. 54, May 1, 1994, pp. 2337-2341.

Choi et al., "EML4-ALK Mutations in Lung Cancer that Confer Resistance to ALK Inhibitors", The New England Journal of Medicine, vol. 18, Oct. 28, 2010, pp. 1734-1739.

CN201580081843.1, "Notice of Decision to Grant", May 26, 2021, 2 pages.

CN201580081843.1, "Office Action", Dec. 7, 2020, 25 pages.

CN201780014376.X, "Notice of Decision to Grant", Jul. 7, 2022, 2 pages.

CN201780014376.X, "Office Action", Apr. 28, 2021, 12 pages.

CN201780014376.X, "Office Action", Jan. 13, 2022, 4 pages.

(56)            References Cited

OTHER PUBLICATIONS

Concepcion et al., "Label-Free Detection of Biomolecular Interactions Using BioLayer Interferometry for Kinetic Characterization", Combinatorial Chemistry and High Throughput Screening, vol. 12, No. 8, Sep. 2009, pp. 791-800.

Crumpacker, "Mechanism of Action of Foscarnet Against Viral Polymerase", American Journal of Medicine, vol. 92, No. 2, Supplement 2A, Feb. 14, 1992, pp. 2A-3S-2A-7S.

Datta et al., "Salt Dependence of DNA Binding by Thermus Aquaticus and Escherichia coli DNA Polymerases", Journal of Biological Chemistry, vol. 278, No. 8, Feb. 21, 2003, pp. 5694-5701.

Deredge et al., "The Glutamate Effect on DNA Binding by Pol I DNA Polymerases: Osmotic Stress and the Effective Reversal of Salt Linkage", Journal of Molecular Biology, vol. 401, No. 2, Aug. 13, 2010, pp. 223-238.

Doublie et al., "An Open and Closed Case for All Polymerases", Structure, vol. 7, No. 2, Feb. 1999, pp. R31-R35.

Dunlap et al., "Use of 2-Aminopurine and Tryptophan Fluorescence as Probes in Kinetic Analyses of DNA Polymerase β", Biochemistry, vol. 41, No. 37, Sep. 17, 2002, pp. 11226-11235.

Dzantiev et al., "A Conformational Change in E. coli DNA Polymerase I (Klenow Fragment) is Induced in the Presence of a dNTP Complementary to the Template Base in the Active Site", Biochemistry, vol. 39, No. 2, Jan. 18, 2000, pp. 356-361.

Engstrom et al., "A Label-Free Continuous Total-Internal-Reflection-Fluorescence-Based Immunosensor", Analytical Biochemistry, vol. 357, No. 2, Oct. 15, 2006, pp. 159-166.

EP15745338.2, "Notice of Decision to Grant", May 4, 2020, 2 pages.

EP15745338.2, "Office Action", Nov. 14, 2018, 4 pages.

EP15745338.2, "Office Action", Nov. 21, 2019, 4 pages.

EP15745338.2, "Office Action", Jul. 15, 2019, 5 pages.

EP17720996.2, "Notice of Decision to Grant", Aug. 11, 2022, 2 pages.

EP17720996.2, "Office Action", Jan. 8, 2020, 4 pages.

EP17720996.2, "Office Action", Aug. 31, 2020, 5 pages.

EP17720996.2, "Office Action", Feb. 22, 2021, 8 pages.

Eriksson et al., "Pyrophosphate Analogues as Inhibitors of DNA Polymerases of Cytomegalovirus, Herpes Simplex Virus and Cellular Origin", Biochimica et Biophysica Acta, vol. 696, No. 2, Feb. 26, 1982, pp. 115-123.

Escobedo et al., "Integrated Nanohole Array Surface Plasmon Resonance Sensing Device Using a Dual-Wavelength Source", Journal of Micromechanics and Microengineering, vol. 21, No. 11, Oct. 2011, pp. 1-6.

Espinoza-Herrera et al., "Following DNA Chain Extension and Protein Conformational Changes in Crystals of a Y-Family DNA Polymerase by Raman Crystallography", Biochemistry, vol. 52, No. 29, Jul. 23, 2013, 22 pages.

Fang et al., "Genome-Wide Mapping of Methylated Adenine Residues in Pathogenic Escherichia coli Using Single-Molecule Real-Time Sequencing", Nature Biotechnology, vol. 30, No. 12, Dec. 2012, pp. 1232-1243.

Favicchio et al., "Fluorescence Spectroscopy and Anisotropy in the Analysis of DNA-Protein Interactions", Methods in Molecular Biology, vol. 543, Feb. 2009, pp. 589-611.

Federley, "New Insights into the Mechanism of DNA Replication on Unmodified and Benzo[a]pyrene Modified Templates Using Surface Plasmon Resonance", Wayne State University Dissertations, Paper 235, Jan. 2011, 208 pages.

Fuller et al., "The Challenges of Sequencing by Synthesis", Nature Biotechnology, vol. 27, No. 11, Nov. 2009, pp. 1013-1023.

Gralla et al., "Potassium Glutamate as a Transcriptional Inhibitor During Bacterial Osmoregulation", The EMBO Journal, vol. 25, No. 7, Apr. 5, 2006, pp. 1515-1521.

Horn et al., "EML4-ALK: Honing in on a New Target in Non-Small-Cell Lung Cancer", Journal of Clinical Oncology, vol. 27, No. 26, Sep. 10, 2009, pp. 4232-4235.

Hoshino et al., "Effect of Ultrasound on DNA Polymerase Reactions: Monitoring on a 27-MHz Quartz Crystal Microbalance", Biomacromolecules, vol. 7, No. 3, Mar. 2006, pp. 682-685.

Hutter et al., "Labeled Nucleoside Triphosphates with Reversibly Terminating Aminoalkoxyl Groups", Nucleosides, Nucleotides and Nucleic Acids, vol. 29, No. 11, Nov. 2010, pp. 879-895.

Jindal et al., "Suramin Affects DNA Synthesis in HeLa Cells by Inhibition of DNA Polymerases", Cancer Research, vol. 50, Dec. 15, 1990, pp. 7754-7757.

Jochmans et al., "Indolopyridones Inhibit Human Immunodeficiency Virus Reverse Transcriptase with a Novel Mechanism of Action", Journal of Virology, vol. 80, No. 24, Dec. 2006, pp. 12283-12292.

JP2018-523734, "Notice of Allowance", May 26, 2020, 3 pages.

JP2018-523734, "Office Action", Sep. 24, 2019, 10 pages.

JP2018-523734, "Office Action", Jan. 22, 2019, 20 pages.

JP2018-538766, "Office Action", Jul. 23, 2019, 10 pages.

JP2018-538766, "Office Action", Mar. 17, 2020, 12 pages.

Kaplan et al., "Photolabile Chelators for the Rapid Photorelease of Divalent Cations", Proceedings of the National Academy of Sciences of the United States of America, vol. 85, Sep. 1988, pp. 6571-6575.

Kaushik et al., "Biochemical Analysis of Catalytically Crucial Aspartate Mutants of Human Immunodeficiency Virus Type 1 Reverse Transcriptase", Biochemistry, vol. 35, No. 36, Sep. 10, 1996, pp. 11536-11546.

Kim et al., "An FET-Type Charge Sensor for Highly Sensitive Detection of DNA Sequence", Biosensors and Bioelectronics, vol. 20, No. 1, Jul. 30, 2004, pp. 69-74.

Klenow et al., "Effect of Monovalent Cations on the Activity of the DNA Polymerase of Escherichia coli B", European Journal of Biochemistry, vol. 9, May 1, 1969, pp. 133-141.

KR10-2018-7024354, "Notice of Final Rejection with Machine Translation", Mar. 26, 2020, 16 pages.

KR10-2018-7024354, "Office Action", Jun. 3, 2020, 17 pages.

KR10-2018-7024354, "Office Action", Sep. 20, 2019, 9 pages.

KR10-2020-7019335, "Notice of Decision to Grant", Mar. 30, 2021, 3 pages.

KR10-2020-7019335, "Office Action", Aug. 27, 2020, 11 pages.

Kumar et al., "Altered Order of Substrate Binding by DNA Polymerase X from African Swine Fever Virus", Biochemistry, vol. 47, No. 30, Jul. 29, 2008, pp. 7875-7887.

Leinbach et al., "Mechanism of Phosphonoacetate Inhibition of Herpesvirus-Induced DNA Polymerase", Biochemistry, vol. 15, No. 2, Jan. 27, 1976, pp. 426-430.

Lutz et al., "An in Vitro Screening Technique for DNA Polymerases that can Incorporate Modified Nucleotides. Pseudo-Thymidine as a Substrate for Thermostable Polymerases", Nucleic Acids Research, vol. 27, No. 13, Jul. 1, 1999, pp. 2792-2798.

Maga et al., "HIV-1 RT Inhibitors with a Novel Mechanism of Action: NNRTIs that Compete with the Nucleotide Substrate", Viruses, vol. 2, No. 4, Apr. 2010, pp. 880-899.

Maga et al., "Selective Interaction of the Human Immunodeficiency Virus Type 1 Reverse Transcriptase Nonnucleoside Inhibitor Efavirenz and its Thio-Substituted Analog with Different Enzyme-Substrate Complexes", Antimicrobial Agents and Chemotherapy, vol. 44, No. 5, May 2000, pp. 1186-1194.

Mano, "Non-Solid Oncogenes in Solid Tumors: EML4-ALK Fusion Genes in Lung Cancer", Cancer Science, vol. 99, No. 12, Dec. 2008, pp. 2349-2355.

Markiewicz et al., "Single-Molecule Microscopy Reveals New Insights into Nucleotide Selection by DNA Polymerase I", Nucleic Acids Research, vol. 40, No. 16, Jun. 4, 2012, pp. 7975-7984.

Masheyekhi et al., "Analysis of Read-Length Limiting Factors in Pyrosequencing Chemistry", Analytical Biochemistry, vol. 363, No. 2, Apr. 15, 2007, 21 pages.

Maxwell et al., "DNA Lesion Alters Global Conformational Dynamics of Y-Family DNA Polymerase During Catalysis", The Journal of Biological Chemistry, vol. 287, No. 16, Apr. 13, 2012, pp. 13040-13047.

Namasivayam et al., "Light-Induced Molecular Cutting: Localized Reaction on a Single DNA Molecule", Analytical Chemistry, vol. 75, No. 16, Aug. 15, 2003, pp. 4188-4194.

(56)                    References Cited

OTHER PUBLICATIONS

Nath et al., "Label Free Colorimetric Biosensing Using Nanoparticles", Journal of Fluorescence, vol. 14, No. 4, Jul. 2004, pp. 377-389.

Nazirizadeh et al., "Low-Cost Label-Free Biosensors Using Photonic Crystals Embedded Between Crossed Polarizers", Optics Express, vol. 18, No. 18, Aug. 30, 2010, pp. 19120-19128.

Nikiforov, "Oligonucleotides Labeled with Single Fluorophores as Sensors for Deoxynucleotide Triphosphate Binding by DNA Polymerases", Analytical Biochemistry, vol. 444, Jan. 1, 2014, pp. 60-66.

Patel et al., "Insights into DNA Polymerization Mechanisms from Structure and Function Analysis of HIV-1 Reverse Transcriptase", Biochemistry, vol. 34, No. 16, Apr. 25, 1995, pp. 5351-5363.

PCT/US2015/041415, "International Search Report and Written Opinion", Feb. 9, 2016, 14 pages.

PCT/US2017/028878, "International Preliminary Report on Patentability", Nov. 1, 2018, 9 pages.

PCT/US2017/028878, "International Search Report and Written Opinion", Aug. 4, 2017, 14 pages.

Peletskaya et al., "Cross-Linking of the Fingers Subdomain of Human Immunodeficiency Virus Type 1 Reverse Transcriptase to Template-Primer", Journal of Virology, vol. 75, No. 19, Oct. 2001, pp. 9435-9445.

Pitta et al., "Synthesis and HIV-1 RT Inhibitory Action of Novel (4/6-Substituted Benzo[d]thiazol-2-yl) Thiazolidin-4-ones. Divergence from the Non-Competitive Inhibition Mechanism", Journal of Enzyme Inhibition and Medicinal Chemistry, vol. 28, No. 1, Feb. 2013, pp. 113-122.

Potapova et al., "Interaction of dNTP, Pyrophosphate and Their Analogs with the dNTP-Binding Sites of E. coli DNA Polymerase I Klenow Fragment and Human DNA Polymerase α", FEBS Letters, vol. 277, Nos. 1-2, Dec. 1990, pp. 194-196.

Previte et al., "DNA Sequencing Using Polymerase Substrate-Binding Kinetics", Nature Communications, vol. 6, No. 5936, Jan. 23, 2015, pp. 1-12.

Puttaswamy, "Optical Method for Measuring Spatial pH Change on Conductive Microelectrodes", Submitted in Fulfillment for the International Master's Program (IMP) Nanomaterials and Nanotechnology KTH, Royal Institute of Technology, Stockholm, Sweden, 2007, pp. 1-66.

Ren et al., "Inhibition of Klenow DNA Polymerase and Poly(A)-Specific Ribonuclease by Aminoglycosides" RNA, vol. 8, No. 11, Nov. 2002, pp. 1393-1400.

Richard et al., "Thermal Stability Landscape for Klenow DNA Polymerase as a Function of pH and Salt Concentration", Biochimica et Biophysica Acta, vol. 1764, No. 10, Oct. 2006, pp. 1546-1552.

Roettger et al., "Mismatched and Matched dNTP Incorporation by DNA Polymerase β Proceed via Analogues Kinetic Pathways", Biochemistry, vol. 47, No. 37, Aug. 22, 2008, pp. 9718-9727.

Santoso et al., "Conformational Transitions in DNA Polymerase I Revealed by Single-Molecule FRET", Proceedings of the National Academy of Sciences, vol. 107, No. 2, Jan. 12, 2010, pp. 715-720.

Schadt et al., "Modeling Kinetic Rate Variation in Third Generation DNA Sequencing Data to Detect Putative Modifications to DNA Bases", Genome Research, vol. 23, No. 1, Jan. 2013, pp. 129-141.

Schultz et al., "Single-Target Molecule Detection with Nonbleaching Multicolor Optical Immunolabels", Proceedings of the National Academy of Sciences of the United States of America, vol. 97, No. 3, Feb. 1, 2000, pp. 996-1001.

Sen et al., "Intrinsic Fluorescence of E. coli RNA Polymerase as a Probe for its Conformational Changes During Transcription Initiation", Biochemical and Biophysical Research Communications, vol. 201, No. 2, Jun. 15, 1994, pp. 820-828.

SG11201807069X, "Written Opinion", Jan. 5, 2021, 7 pages.

SG11201807069X, "Written Opinion", Jul. 15, 2019, 9 pages.

Soda et al., "Identification of the Transforming EML4-ALK Fusion Gene in Non-Small-Cell Lung Cancer", Nature, vol. 448, Aug. 2, 2007, pp. 561-566.

Star et al., "Electronic Detection of Specific Protein Binding Using Nanotube FET Devices", Nano Letters, vol. 3, No. 4, Mar. 5, 2003, 5 pages.

Su et al., "Surface Plasmon Resonance Spectroscopy and Quartz Crystal Microbalance Study of Streptavidin Film Structure Effects on Biotinylated DNA Assembly and Target DNA Hybridization", Langmuir, vol. 21, No. 1, Jan. 4, 2005, pp. 348-353.

Tsai, "Kinetics of DNA Polymerase Conformational Changes During Nucleotide Binding and Incorporation", Dissertation, Presented to the Faculty of the Graduate School of The University of Texas at Austin in Partial Fulfillment of the Requirements for the Degree of Doctor of Philosophy, May 2005, 148 pages.

Tsai et al., "Site-Specific Labeling of T7 DNA Polymerase with a Conformationally Sensitive Fluorophore and its Use in Detecting Single-Nucleotide Polymorphisms", Analytical Biochemistry, vol. 384, No. 1, Jan. 1, 2009, pp. 136-144.

Vaidyanathan et al., "Binary and Ternary Binding Affinities Between Exonuclease-Deficient Klenow Fragment (Kf-exo-) and Various Arylamine DNA Lesions Characterized by Surface Plasmon Resonance", Chemical Research in Toxicology, vol. 25, No. 8, Aug. 20, 2012, 7 pages.

Vaidyanathan et al., "Binding Kinetics of DNA-Protein Interaction Using Surface Plasmon Resonance", Protocol Exchange, May 22, 2013, 11 pages.

Vollmer et al., "Whispering-Gallery-Mode Biosensing: Label-Free Detection Down to Single Molecules", Nature Methods, vol. 5, No. 7, Jul. 2008, pp. 591-596.

Walsh et al., "Synthetic Nucleotides as Probes of DNA Polymerase Specificity", Journal of Nucleic Acids, vol. 2012, Jun. 2012, 17 pages.

Washington et al., "Human DNA Polymerase ιUtilizes Different Nucleotide Incorporation Mechanisms Dependent Upon the Template Base", Molecular and Cellular Biology, vol. 24, No. 2, Jan. 2004, pp. 936-943.

Xia et al., "DNA Mismatch Synthesis Complexes Provide Insights into Base Selectivity of a B Family DNA Polymerase", Journal of the American Chemical Society, vol. 135, No. 1, Jan. 9, 2013, 20 pages.

Yuzenkova et al., "Tagetitoxin Inhibits Transcription by Stabilizing Pre-Translocated State of the Elongation Complex", Nucleic Acids Research, vol. 41, No. 20, Nov. 2013, pp. 1-9.

* cited by examiner

SEQUENCE LISTING

Sequence total quantity: 4
SEQ ID NO: 1                moltype = DNA  length = 90
FEATURE                     Location/Qualifiers -continued

```
misc_feature          1..90
                      note = synthethic phiX oligonucleotide sequence
misc_feature          62..90
                      note = primer binding region
source                1..90
                      mol_type = other DNA
                      organism = synthetic construct
SEQUENCE: 1
agaaggcggt tcctgaatga atgggaagcc ttcaagaagg tgataagcag gagaaacata  60
cgaaggcgca taacgatacc actgaccctc                                    90

SEQ ID NO: 2         moltype = DNA   length = 90
FEATURE              Location/Qualifiers
misc_feature          1..90
                      note = synthethic phiX oligonucleotide sequence
misc_feature          54
                      note = SNP (single-nucleotide polymorphism)
misc_feature          62..90
                      note = primer binding region
source                1..90
                      mol_type = other DNA
                      organism = synthetic construct
SEQUENCE: 2
agaaggcggt tcctgaatga atgggaagcc ttcaagaagg tgataagcag gaggaacata  60
cgaaggcgca taacgatacc actgaccctc                                    90

SEQ ID NO: 3         moltype = DNA   length = 90
FEATURE              Location/Qualifiers
misc_feature          1..90
                      note = synthethic phiX oligonucleotide sequence
misc_feature          51
                      note = SNP (single-nucleotide polymorphism)
misc_feature          62..90
                      note = primer binding region
source                1..90
                      mol_type = other DNA
                      organism = synthetic construct
SEQUENCE: 3
agaaggcggt tcctgaatga atgggaagcc ttcaagaagg tgataagcag aagaaacata  60
cgaaggcgca taacgatacc actgaccctc                                    90

SEQ ID NO: 4         moltype = DNA   length = 29
FEATURE              Location/Qualifiers
misc_feature          1..29
                      note = synthethic phiX oligonucleotide sequence
misc_feature          1
                      note = 5' Guanine labeled with biotin (5Biosg)
source                1..29
                      mol_type = other DNA
                      organism = synthetic construct
SEQUENCE: 4
gaaggcgcat aacgatacca ctgaccctc                                     29
```

DISTINGUISHING SEQUENCES BY DETECTING POLYMERASE DISSOCIATION

CROSS-REFERENCE TO RELATED APPLICATION

This application is a continuation of U.S. application Ser. No. 16/486,062, filed Aug. 14, 2019, which is the National Stage Application of International Application No. PCT/US2018/018118, filed Feb. 14, 2018, which claims priority to U.S. Provisional Application No. 62/459,437, filed Feb. 15, 2017, which are incorporated by reference herein in their entirety.

SEQUENCE LISTING

A Sequence Listing conforming to the rules of WIPO Standard ST.26 is hereby incorporated by reference. The Sequence Listing has been filed as an electronic document via EFS-Web in XML code. The electronic document, created on Sep. 23, 2022, is entitled "097128-1348887-034US2_ST26.xml", and is 8,651 bytes in size.

BACKGROUND

The present disclosure relates generally to molecular diagnostics, and has specific applicability to evaluation of nucleic acids.

Small differences in nucleic acid sequences can result in significant differences in biological function. For example, single nucleotide polymorphisms (SNPs) in the human genome underlie differences in susceptibility to disease. A wide range of human diseases, such as sickle-cell anemia, β-thalassemia, Alzheimer's Disease and cystic fibrosis result from SNPs. Recent advances in genotyping and DNA sequencing have identified many SNPs that are associated with the probability of developing a variety of diseases and conditions. Such SNPs can be useful for diagnosis and prognosis of the disease or conditions to which they have been associated. Furthermore, many of these SNPs are likely to be therapeutically relevant genetic variants and/or involved in genetic predisposition to disease. However, accurate diagnostic correlations generally require evaluation of large SNP panels (e.g. on a genome-wide scale) for a large population of individuals. Currently available methods are costly and time consuming, which is unfavorable for scaling the methods to clinically meaningful levels.

Thus, there exists a need for efficient methods to detect a large variety of SNPs, or other nucleic acid polymorphisms, often in many individuals. The present disclosure satisfies this need and provides related advantages as well.

BRIEF SUMMARY

The present disclosure provides a method for determining the presence of a nucleic acid allele. The method can include the steps of (a) binding a polymerase to a double stranded nucleic acid that includes a primer hybridized to a template, the template including a first allele of a locus; (b) adding a nucleotide to the primer via catalytic activity of the polymerase, thereby producing an extended double stranded nucleic acid; (c) dissociating the polymerase from the extended double stranded nucleic acid; (d) detecting dissociation of the polymerase from the extended double stranded nucleic acid; and (e) comparing the dissociation of the polymerase from the extended double stranded nucleic acid to dissociation of the polymerase from a second double stranded nucleic acid, the second double stranded nucleic acid including a primer hybridized to the same position of the locus as the primer of the extended double stranded nucleic acid, thereby determining the presence of the first allele in the template nucleic acid.

Additionally, a method is provided for distinguishing nucleic acid alleles by carrying out the steps of (a) providing a first template nucleic acid including a first allele of a locus and a second template nucleic acid including a second allele of the locus, wherein the first and second templates are hybridized to a primer, thereby providing first and second double stranded nucleic acids, respectively; (b) binding polymerases to the first and second double stranded nucleic acids; (c) adding nucleotides to the primers of the first and second double stranded nucleic acids via catalytic activity of the polymerases, thereby producing an extended first double stranded nucleic acid and an extended second double stranded nucleic acid; (d) dissociating the polymerases from the extended double stranded nucleic acids; (e) detecting dissociation of the polymerase from the extended double stranded nucleic acids; and (f) determining a difference in the dissociation of the polymerase from the first extended double stranded nucleic acid to the dissociation of the polymerase from the second extended double stranded nucleic acid, thereby distinguishing the first allele from the second allele.

DETAILED DESCRIPTION

Figure 1A:
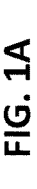
FIG. 1A is a graph showing a plot of initial dissociation rates measured during incorporation/dissociation steps for each cycle of a Sequencing By Binding' run performed with a PhiX wild type template and the PhiX m2 mutant.

The present disclosure provides methods for detecting or identifying sequence variants such as target alleles of interest. Particular embodiments of the methods set forth herein exploit the surprising observation that the rate at which a polymerase dissociates from a primed template nucleic acid following primer extension is influenced by the sequence of the nucleic acid. The dissociation rate can be detected in a way to distinguish different sequences such as different alleles at a locus. For example, a polymerase can extend a primer that is hybridized to a test template such that a single nucleotide is added, the nucleotide being the cognate for an allelic position in a locus that is present in the template. Then the polymerase can be dissociated from the extended test nucleic acid and the dissociation can be detected and compared to the dissociation of the polymerase from a control nucleic acid. In particular cases, the control nucleic acid is a template having the same or different allele as the test template and a primer that is hybridized to this control template at a position that is the same as the position that is primer hybridized in the test template. The similarity or difference between the dissociations for the test and control nucleic acid can be used to determine the similarity or difference, respectively, for the alleles present in the test and control templates.

An advantage of some embodiments of the present methods is that comparative dissociation characteristics (e.g. dissociation rates) allow a target allele to be distinguished from other nucleic acids, including for example, other alleles that differ from the target allele, in some cases by only a single nucleotide. In some embodiments, a nucleotide that is added to a primer can be identified, for example, via a detection step used in a nucleic acid sequencing technique. The dissociation of the polymerase from the extended nucleic acid can be detected as well. The combined information from the sequencing detection step and dissociation measurement can be used to obtain a higher level of confidence in identifying the sequence of the template than would be available from only one of the two detection steps. For example, comparative dissociation characteristics can be used as an error check for a nucleotide call made by a sequencing detection step. Moreover, repetitive cycles of detecting extension products of a sequencing step followed by detecting dissociation characteristics can be used to obtain a more accurate sequence than would be available absent the dissociation rate measurements.

In particular embodiments, the present disclosure provides methods for distinguishing variants in a nucleic acid template that are difficult to distinguish when sequencing under homopolymer compression conditions. Homopolymer compression occurs, for example, when preforming an extension-based sequencing technique using extendible nucleotides (e.g., sequencing by synthesis or pyrosequencing using nucleotides that lack reversible terminator moieties). In such cases, the number of nucleotides added to a primer during a single sequencing cycle will be correlated with the length of a homopolymer region that is primed for extension. Often it is difficult to accurately identify the number of nucleotides that were added due to limitations in the dynamic range or linearity of signal acquisition for the sequencing methods. The resulting sequence is often referred to as being homopolymer compressed. The comparative dissociation methods set forth herein can be employed to distinguish homopolymers that differ by as few as one nucleotide. Thus, the methods can be used to add single nucleotide resolution to particular positions (e.g., positions near the end of a homopolymer region) in a homopolymer compressed sequence.

Terms used herein will be understood to take on their ordinary meaning in the relevant art unless specified otherwise. Several terms used herein and their meanings are set forth below.

As used herein, the term "adjacent," when used in reference to two nucleotides in a sequence, means one of the nucleotides immediately follows the other nucleotide in the sequence. Accordingly, adjacent nucleotides are covalently linked to each other in the sequence. In contrast, two nucleotides that are near each other can, optionally, be separated by one or a few intervening nucleotides in the sequence.

As used herein, the term "allele," when used in reference to a locus in a nucleic acid, refers to any of the alternative nucleotides, sequences or genetic features that occur at the locus. Exemplary alleles include, but are not limited to single nucleotide polymorphisms (SNPs), insertions and/or deletions (indels), alternative mRNA splice sites, mutations (whether naturally occurring or engineered by human intervention), sequence variants, or repeats that occur at a locus. An allele can, but need not, have a known biological function.

As used herein, the term "array" refers to a population of molecules that are attached to one or more solid-phase substrates such that the molecules at one feature can be distinguished from molecules at other features. An array can include different molecules that are each located at different addressable features on a solid-phase substrate. Alternatively, an array can include separate solid-phase substrates each functioning as a feature that bears a different molecule, wherein the different probe molecules can be identified according to the locations of the solid-phase substrates on a surface to which the solid-phase substrates are attached, or according to the locations of the solid-phase substrates in a liquid such as a fluid stream. The molecules of the array can be nucleotides, nucleic acid primers, nucleic acid probes, nucleic acid templates or nucleic acid enzymes such as polymerases, ligases or exonucleases.

As used herein, a "blocking moiety," when used with reference to a nucleotide analog, is a part of the nucleotide that inhibits or prevents the nucleotide from forming a covalent linkage to a second nucleotide (e.g., via the 3'-OH of a primer nucleotide) during the incorporation step of a nucleic acid polymerization reaction. The blocking moiety of a "reversible terminator" nucleotide can be removed from the nucleotide analog, or otherwise modified, to allow the 3'-OH of the nucleotide to covalently link to a second nucleotide. Such a blocking moiety is referred to herein as a "reversible terminator moiety." Exemplary reversible terminator moieties are set forth in U.S. Pat. Nos. 7,427,673; 7,414,116; 7,057,026 and PCT publications WO 91/06678 and WO 07/123744, each of which is incorporated by reference.

As used herein, the term "comprising" is intended herein to be open-ended, including not only the recited elements, but further encompassing any additional elements.

As used herein, the term "dissociate," when used in reference to a molecule that is bound to something, refers to the disconnection or separation of the molecule from the thing. For example, one or more of the components of a ternary complex (e.g. a primed template, polymerase or nucleotide) can be removed from the other members of the complex by dissociation. In particular embodiments, a molecule is bound via non-covalent linkages that are disrupted to cause dissociation.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "exogenous," when used in reference to a moiety of a molecule, means a moiety that is not present in a natural analog of the molecule. For example, an exogenous label of a nucleotide is a label that is not present on a naturally occurring nucleotide. Similarly, an exogenous label that is present on a polymerase is not found on the polymerase in its native milieu.

As used herein, the term "extended," when used in reference to a nucleic acid, means the product of adding one or more nucleotide moieties to the 3' end of the nucleic acid. An extended nucleic acid can have at least 1, 2, 3, 4, 5, 10, 25, 50, 100 or more nucleotides added to the 3' end. Alternatively or additionally, an extended nucleic acid can have at most 100, 50, 25, 10, 5, 4, 3, 2 or 1 nucleotides added to the 3' end. As used herein, the term "serially extended," when used in reference to a nucleic acid, means the product of adding two or more nucleotide moieties to the 3' end of the nucleic acid. A serially extended nucleic acid can have at least 2, 3, 4, 5, 10, 25, 50, 100 or more nucleotides added to the 3' end. Alternatively or additionally, a serially extended nucleic acid can have at most 100, 50, 25, 10, 5, 4, 3 or 2 nucleotides added to the 3' end.

As used herein, the term "extension," when used in reference to a nucleic acid, refers to a process of adding at least one nucleotide to the 3' end of the nucleic acid. A nucleotide that is added to a nucleic acid by extension is said to be incorporated into the nucleic acid. Accordingly, the term "incorporating" can be used to refer to the process of joining a nucleotide to the 3' end of a nucleic acid by formation of a phosphodiester bond.

As used herein, the term "feature" means a location in an array where a particular molecule is present. A feature can contain only a single molecule or it can contain a population of several molecules of the same species. Alternatively, a feature can include a population of molecules that are different species (e.g. a population of ternary complexes having different template sequences). Features of an array are typically discrete. The discrete features can be contiguous or they can have spaces between each other. An array useful herein can have, for example, features that are separated by less than 100 micron, 50 micron, 10 micron, 5 micron, 1 micron, or 0.5 micron. Alternatively or additionally, an array can have features that are separated by greater than 0.5 micron, 1 micron, 5 micron, 10 micron, 50 micron or 100 micron. The features can each have an area of less than 1 square millimeter, 500 square micron, 100 square micron, 25 square micron, 1 square micron or less.

As used herein, the term "homopolymer" refers to a contiguous sequence of two or more nucleotides of one type. For example, a homopolymer can include at least 2 adenine nucleotides in a row, at least 2 thiamine nucleotides in a row, at least 2 guanine nucleotides in a row, at least 2 cytosine nucleotides in a row or at least 2 uracil nucleotides in a row. A homopolymer can include, for example, at least 2, 3, 4, 5, 8, 10, 12, 15, 20 or more nucleotides in a row.

The term "locus," when used in reference to a nucleic acid, refers to the position in the nucleic acid where a nucleotide, nucleic acid sequence, indel, or genetic feature occurs. One or more positions within a locus can be known or suspected to vary in a sample such that two or more alleles are observed or suspected. A locus can, but need not, have a known biological function.

As used herein, the term "next correct nucleotide" refers to the nucleotide type that will bind and/or incorporate at the 3' end of a primer to complement a base in a template strand to which the primer is hybridized. The base in the template strand is referred to as the "next template nucleotide" and is immediately 5' of the base in the template that is hybridized to the 3' end of the primer. The next correct nucleotide can be referred to as the "cognate" of the next template nucleotide and vice versa. Cognate nucleotides that interact with each other in a ternary complex or in a double stranded nucleic acid are said to "pair" with each other. A nucleotide having a base that is not complementary to the next template base is referred to as an "incorrect", "mismatch" or "noncognate" nucleotide.

As used herein, the term "nucleotide" can be used to refer to a native nucleotide or analog thereof. Examples include, but are not limited to, nucleotide triphosphates (NTPs) such as ribonucleotide triphosphates (rNTPs), deoxyribonucleotide triphosphates (dNTPs), or analogs thereof such as dideoxyribonucleotide triphosphates (ddNTPs) or reversibly terminated nucleotide triphosphates (rtNTPs). Other nucleotides include nucleotide monophosphates (NMPs), and analogs thereof.

As used herein, the term "polymerase" can be used to refer to a nucleic acid synthesizing enzyme, including but not limited to, DNA polymerase, RNA polymerase, reverse transcriptase, primase and transferase. Typically, the polymerase has one or more active sites at which nucleotide binding and/or catalysis of nucleotide polymerization may occur. The polymerase may catalyze the polymerization of nucleotides to the 3' end of the first strand of the double stranded nucleic acid molecule. For example, a polymerase catalyzes the addition of a next correct nucleotide to the 3' OH group of the first strand of the double stranded nucleic acid molecule via a phosphodiester bond, thereby covalently incorporating the nucleotide to the first strand of the double stranded nucleic acid molecule. Optionally, a polymerase need not be capable of nucleotide incorporation under one or more conditions used in a method set forth herein. For example, a mutant polymerase may be capable of forming a ternary complex but incapable of catalyzing nucleotide incorporation.

As used herein, the term "sequencing-by-binding" refers to a sequencing technique wherein specific binding of a polymerase and cognate nucleotide to a primed template nucleic acid molecule is used for identifying the next correct nucleotide to be incorporated into the primer strand of the primed template nucleic acid molecule. The specific binding interaction need not result in chemical incorporation of the nucleotide into the primer. In some embodiments, the specific binding interaction can precede chemical incorporation of the nucleotide into the primer strand or can precede chemical incorporation of an analogous, next correct nucleotide into the primer. Thus, detection of the next correct nucleotide can take place prior to incorporation of the next correct nucleotide or without incorporation of the next correct nucleotide.

As used herein, the term "sequencing-by-synthesis" refers to a sequencing technique wherein the 3' end of a template-bound primer is extended and one or more products of the extension reaction are detected to determine the sequence of the template. In some embodiments, a polymerase catalyzes addition of individual nucleotides to the primer by extension. For example, reversibly blocked nucleotides can be added serially to a primer through cycles of single base extension and deblocking to remove blocking moieties from the extended primer. In some embodiments, the nucleotides that are added by polymerase catalysis are labeled. However, the nucleotides need not be labeled, for example, in pyrosequencing techniques where pyrophosphate that is produced by nucleotide incorporation is detected (e.g. 454 sequencing commercially available from Roche, Basel Switzerland), or techniques where a proton that is produced by nucleotide incorporation is detected (e.g. Ion Torrent sequencing commercially available from Thermo Fisher, Waltham, MA). In alternative embodiments, oligonucleotides are added to the primer by extension such that the extended primer grows by more than one nucleotide at a time. Methods that add oligonucleotides can also be referred to as "sequencing by ligation" techniques.

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers.

As used herein, the term "ternary complex" refers to an intermolecular association between a polymerase, a double stranded nucleic acid and a nucleotide. Typically, the polymerase facilitates interaction between a next correct nucleotide and a template strand of the primed nucleic acid. A next correct nucleotide can interact with the template strand via Watson-Crick hydrogen bonding. The term "stabilized ternary complex" means a ternary complex having promoted or prolonged existence or a ternary complex for which disruption has been inhibited. Generally, stabilization of the ternary complex prevents incorporation of the nucleotide component of the ternary complex into the primed nucleic acid component of the ternary complex.

As used herein, the term "rate" is intended to be consistent with the meaning of the term as it is known in the art of enzyme kinetics, for example, as described in Segel, *Enzyme Kinetics* John Wiley and Sons, New York (1975), which is incorporated herein by reference. These terms can be used to describe any of a variety of interactions that occur in a particular reaction between polymerase, nucleotide and nucleic acid. For example, the term can be used to characterize pair-wise interactions that occur during association or dissociation of a larger complex such as the pair-wise interaction between polymerase and template nucleic acid in a complex that forms between the polymerase, template and a monomeric nucleotide. The term can also characterize a combination or series of interactions such as interactions between polymerase, template nucleic acid and a nucleotide that form a ternary complex.

The embodiments set forth below and recited in the claims can be understood in view of the above definitions.

The present disclosure provides a method for determining the presence of a nucleic acid allele. The method can include steps of (a) binding a polymerase to a double stranded nucleic acid that includes a primer hybridized to a template, the template including a first allele of a locus; (b) adding a nucleotide to the primer via catalytic activity of the polymerase, thereby producing an extended double stranded nucleic acid; (c) dissociating the polymerase from the extended double stranded nucleic acid; (d) detecting dissociation of the polymerase from the extended double stranded nucleic acid; and (e) comparing the dissociation of the polymerase from the extended double stranded nucleic acid to dissociation of the polymerase from a second double stranded nucleic acid, the second double stranded nucleic acid including a primer hybridized to the same position of the locus as the primer of the extended double stranded nucleic acid, thereby determining the presence of the first allele in the template nucleic acid.

A method set forth herein can include a step of comparing the dissociation of a polymerase from a first nucleic acid to the dissociation of the polymerase from a second nucleic acid. Any of a variety of dissociation characteristics can be detected and compared in a method set forth herein. For example, dissociation rates can be detected and compared. Other characteristics include, but are not limited to, time-series parameterizations such as curves fitted to dissociation data, wherein exponential amplitude or rate determined from the curve can be used for classification.

In some embodiments, dissociation is detected between polymerase and a first nucleic acid having a primer that is hybridized to a locus in a first template and dissociation is detected between polymerase and a second nucleic acid that includes a primer that is hybridized to a second template having the same locus. The second template can include the same allele as the first template or, alternatively, a different allele. For example, the first and second templates can have the same allele and a similarity in the rate at which the polymerase dissociates from the first nucleic acid to a rate at which the polymerase dissociates from the second nucleic acid can be determined. In an alternative example, the first and second templates can have different alleles at a locus and a difference in the rate at which the polymerase dissociates from the first nucleic acid to a rate at which the polymerase dissociates from the second nucleic acid can be determined.

In some embodiments, dissociation of polymerase from the first and second nucleic acids is performed separately. For example, dissociation of polymerase from the second nucleic acid can be determined prior to detecting dissociation from the first nucleic acid. The data from the second nucleic acid can be stored (e.g. in an electronic database or other computer readable medium) and used for comparison after obtaining data for the first nucleic acid. Thus, the methods of distinguishing target sequences set forth herein can be used to identify a target sequence based on comparison to a known reference sequence.

In alternative embodiments, two templates can be distinguished (or shown to be the same) based on data obtained by performing extension and/or dissociation steps in parallel for the two templates. Accordingly, a method is provided for distinguishing nucleic acid alleles by carrying out the steps of (a) providing a first template nucleic acid including a first allele of a locus and a second template nucleic acid including a second allele of the locus, wherein the first and second templates are hybridized to a primer, thereby providing first and second double stranded nucleic acids, respectively; (b) binding polymerases to the first and second double stranded nucleic acids; (c) adding nucleotides to the primers of the first and second double stranded nucleic acids via catalytic activity of the polymerases, thereby producing an extended first double stranded nucleic acid and an extended second double stranded nucleic acid; (d) dissociating the polymerases from the extended double stranded nucleic acids; (e) detecting dissociation of the polymerase from the extended double stranded nucleic acids; and (0 determining a difference in the dissociation of the polymerase from the first extended double stranded nucleic acid to the dissociation of the polymerase from the second extended double stranded nucleic acid, thereby distinguishing the first allele from the second allele.

Nucleic acid templates that are used in a method or composition herein can be DNA such as genomic DNA, synthetic DNA, amplified DNA, complementary DNA (cDNA) or the like. RNA can also be used such as mRNA, ribosomal RNA, tRNA or the like. Nucleic acid analogs can also be used as templates herein. Thus, a mixture of nucleic acids used herein can be derived from a biological source, synthetic source or amplification reaction. Primers used herein can be DNA, RNA or analogs thereof.

Particularly useful nucleic acid templates are genome fragments that include sequences identical to a portion of a genome. A population of genome fragments can include at least 5%, 10%, 20%, 30%, 40%, 50%, 60%, 70%, 75%, 80%, 85%, 90%, 95% or 99% of a genome. A genome fragment can have, for example, a sequence that is substantially identical to at least about 25, 50, 70, 100, 200, 300, 400, 500, 600, 700, 800, 900 or 1000 or more nucleotides of a genome. A genome fragment can be DNA, RNA, or an analog thereof.

Exemplary organisms from which nucleic acids can be derived include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a dictyostelium discoideum; a fungi such as *Pneumocystis carinii*, Takifugu rubripes, yeast, *Saccharamoyces cerevisiae* or Schizosaccharomyces pombe; or a *Plasmodium falciparum*. Nucleic acids can also be derived from a prokaryote such as a bacterium, *Escherichia coli*, staphylococci or *Mycoplasma pneumoniae*; an archae; a virus such as Hepatitis C virus or human immunodeficiency virus; or a viroid. Nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual, 3rd edition*, Cold Spring Harbor Laboratory, New York (2001) or in Ausubel et al., *Current Protocols in Molecular Biology*, John Wiley and Sons, Baltimore, Md. (1998), each of which is incorporated herein by reference.

A template nucleic acid can be obtained from a preparative method such as genome isolation, genome fragmentation, gene cloning and/or amplification. Such procedures are known by those skilled in the art. Some exemplary techniques include DNA purification by phenol extraction (see, e.g., Sambrook et al., Molecular Cloning: A Laboratory Manual. New York: Cold Spring Harbor Press, 1989), partial purification by salt precipitation (see, e.g., Miller et al., *Nucl Acids Res*, 1988, 16:1215) or chelex (see, e.g., Walsh et al., Biotechniques, 1991, 10:506-513; Comey et al., *J Forensic Sci*, 1994, 39:1254) and PCR amplification methods (see, e.g., Burckhardt, *PCR Methods and Applications*, 1994, 3:239-243; McCabe, *PCR Methods and Applications*, 1991, 1:99-106; Nordvag, *Biotechniques*, 1992, 12(4): 490-492).

It will be understood that PCR amplification methods such as those set forth above and elsewhere herein are exemplary. Any of a variety of known amplification techniques can be used to increase the amount of nucleic acid sequences present for use in a method set forth herein. Exemplary techniques include, but are not limited to, polymerase chain reaction (PCR), rolling circle amplification (RCA), multiple displacement amplification (MDA), or random prime amplification (RPA) of nucleic acid molecules having template sequences. It will be understood that amplification of nucleic acids prior to use in a method or composition set forth herein is optional. As such, template nucleic acids will not be amplified prior to use in some embodiments of the methods and compositions set forth herein. Solid-phase amplification methods can also be used, including for example, cluster amplification, bridge amplification, solid-phase PCR, solid-phase RCA, solid-phase MDA or other methods that utilize support-bound primers to capture and/or prime synthesis of nucleic acids. Rolling circle amplification (RCA) can be carried out, for example, as described in Lizardi et al., *Nat. Genet.* 19:225-232 (1998) or U.S. Pat. App. Pub. No. 2007/0099208 A1, each of which is incorporated herein by reference. Exemplary methods for cluster amplification are set forth, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No.

2007/0128624; and U.S. Patent Publ. No. 2008/0009420, each of which is incorporated herein by reference. Further useful methods for isolating, amplifying and fragmenting nucleic acids include those used to produce templates for analysis on microarrays such as those set forth in U.S. Pat. No. 6,355,431 or U.S. Pat. No. 9,045,796, each of which is incorporated herein by reference. Amplification can also be carried out using a method set forth in Sambrook et al., *Molecular Cloning: A Laboratory Manual, 3rd edition*, Cold Spring Harbor Laboratory, New York (2001) or in Ausubel et al., *Current Protocols in Molecular Biology*, John Wiley and Sons, Baltimore, Md. (1998), each of which is incorporated herein by reference.

Several embodiments of the methods set forth herein are exemplified with respect to identifying or distinguishing alleles at a particular locus. However, in some embodiments, template nucleic acids evaluated in a method set forth herein can be different loci of a single genome. As such, the methods can be used to identify genetic regions of interest within an individual's genome. The template sequences can be from different individuals of the same species. In this case, the methods can be used to identify, distinguish or characterize individuals. For example, the methods can be used in a diagnostic or forensic capacity. The template sequences can be from different species of organism. As such, the methods can be used to identify, distinguish or characterize types of organisms. For example, the methods can be used to detect pathogens or diagnose individuals suspected of being infected with a pathogen, or the methods can be used for metagenomic analysis such as evaluation of the flora of the human digestive system.

Polymerases that may be used to carry out a method of the present disclosure include naturally occurring polymerases and modified variations thereof, including, but not limited to, mutants, recombinants, fusions, genetic modifications, chemical modifications, synthetics, and analogs. Naturally occurring polymerases and modified variations thereof are not limited to polymerases that have the ability to catalyze a polymerization reaction. For example, a non-catalytically active polymerase that retains binding specificity can be used in a step where ternary complex is formed and examined in order to assist in identifying the next correct nucleotide for the primed template upon which the ternary complex forms. Optionally, the naturally occurring and/or modified variations thereof have the ability to catalyze a polymerization reaction. Optionally, the naturally-occurring and/or modified variations have modified properties, for example, enhanced binding affinity to nucleic acids, reduced binding affinity to nucleic acids, enhanced binding affinity to nucleotides, reduced binding affinity to nucleotides, enhanced specificity for next correct nucleotides, reduced specificity for next correct nucleotides, enhanced catalysis rates, reduced catalysis rates, catalytic inactivity etc. Mutant polymerases include, for example, polymerases wherein one or more amino acids are replaced with other amino acids, or insertions or deletions of one or more amino acids.

Modified polymerases include polymerases that contain an exogenous label moiety (e.g., an exogenous fluorophore), which can be used to detect the polymerase. For example, the rate at which a polymerase dissociates from a nucleic acid can be determined from loss of signal at a feature of an array where labeled polymerase interacts with a feature-bound nucleic acid. Optionally, the label moiety can be attached after the polymerase has been at least partially purified using protein isolation techniques. For example, the exogenous label moiety can be chemically linked to the polymerase using a free sulfhydryl or a free amine moiety of the polymerase. This can involve chemical linkage to the polymerase through the side chain of a cysteine residue, or through the free amino group of the N-terminus. An exogenous label moiety can also be attached to a polymerase via protein fusion. Exemplary label moieties that can be attached via protein fusion include, for example, green fluorescent protein (GFP) or wavelength shifted variants of GFP.

Useful DNA polymerases include, but are not limited to, bacterial DNA polymerases, eukaryotic DNA polymerases, archaeal DNA polymerases, viral DNA polymerases and phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases α, β, γ, δ, ε, η, ζ, λ, δ, μ, and k, as well as the Revl polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cpl DNA polymerase, T7 DNA polymerase, and T4 polymerase. Other useful DNA polymerases include thermostable and/or thermophilic DNA polymerases such as *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occullum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. Engineered and modified polymerases also are useful in connection with the disclosed techniques. For example, modified versions of the extremely thermophilic marine archaea *Thermococcus* species 9° N (e.g., Therminator DNA polymerase from New England BioLabs Inc.; Ipswich, MA) can be used. Still other useful DNA polymerases, including the 3PDX polymerase are disclosed in U.S. Pat. No. 8,703,461, the disclosure of which is incorporated herein by reference.

Useful RNA polymerases include, but are not limited to, viral RNA polymerases such as T7 RNA polymerase, T3 polymerase, SP6 polymerase, and Kll polymerase; Eukaryotic RNA polymerases such as RNA polymerase I, RNA polymerase II, RNA polymerase III, RNA polymerase IV, and RNA polymerase V; and Archaea RNA polymerase.

Useful reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase that maintains the telomeres of eukaryotic chromosomes.

A polymerase having an intrinsic 3'-5' proofreading exonuclease activity can be useful for some embodiments. Polymerases that substantially lack 3'-5' proofreading exonuclease activity are also useful in some embodiments, for example, in most sequencing embodiments. Absence of exonuclease activity can be a wild type characteristic or a characteristic imparted by a variant or engineered polymerase structure. For example, exo minus Klenow fragment is a mutated version of Klenow fragment that lacks 3'-5' proofreading exonuclease activity. Klenow fragment and its exo minus variant can be useful in a method or composition set forth herein.

Particular embodiments of the methods set forth herein can use a native nucleotide, nucleotide analog or modified nucleotide. Such nucleotides can be used, for example, for forming a ternary complex and, optionally, for polymerase catalyzed incorporation into a template-bound primer. Optionally, a nucleotide analog has a nitrogenous base, five-carbon sugar, and phosphate group; wherein any moiety of the nucleotide may be modified, removed and/or replaced. Nucleotide analogs that are used to form stabilized ternary complexes may be non-incorporable nucleotides. Such nucleotides that are incapable of incorporation include, for example, monophosphate and diphosphate nucleotides. In another example, the nucleotide may contain modification(s) to the triphosphate group that make the nucleotide nonincorporable. Examples of non-incorporable nucleotides may be found in U.S. Pat. No. 7,482,120, which is incorporated by reference herein. In some embodiments, nonincorporable nucleotides may be subsequently modified to become incorporable. Non-incorporable, nucleotide analogs include, but are not limited to, alpha-phosphate modified nucleotides, alpha-beta nucleotide analogs, beta-phosphate modified nucleotides, beta-gamma nucleotide analogs, gamma-phosphate modified nucleotides, caged nucleotides, or ddNTPs.

Nucleotide analogs can include terminators that reversibly prevent nucleotide incorporation at the 3'-end of the primer after the analog has been incorporated. For example, U.S. Pat. Nos. 7,544,794 and 8,034,923 (the disclosures of these patents are incorporated herein by reference) describe reversible terminators in which the 3'-OH group is replaced by a 3'-ONH$_2$ moiety. Another type of reversible terminator is linked to the nitrogenous base of a nucleotide, for example, as set forth in U.S. Pat. No. 8,808,989 (the disclosure of which is incorporated herein by reference). Other reversible terminators that similarly can be used in connection with the methods described herein include those described in U.S. Pat. Nos. 7,956,171, 8,071,755, and 9,399, 798 (the disclosures of these U.S. patents are incorporated herein by reference). In certain embodiments, a reversible blocking moiety can be removed from a primer, allowing for nucleotide incorporation. Compositions and methods for deblocking are set forth in the above references.

Alternatively, nucleotide analogs irreversibly prevent nucleotide incorporation at the 3'-end of the primer to which they have been incorporated. Irreversible nucleotide analogs include 2', 3'-dideoxynucleotides (ddNTPs such as ddGTP, ddATP, ddTTP, ddCTP). Dideoxynucleotides lack the 3'-OH group of dNTPs that is essential for polymerase-mediated primer extension.

Optionally, a nucleotide (e.g. a native nucleotide or nucleotide analog) is present in a mixture during a step of a method set forth herein. For example, at least 1, 2, 3, 4 or more nucleotide types can be simultaneously present. Alternatively or additionally, at most 4, 3, 2, or 1 nucleotide types can be simultaneously present. Similarly, one or more nucleotide types that are simultaneously present can be complementary to at least 1, 2, 3 or 4 nucleotide types in a template nucleic acid. Alternatively or additionally, one or more nucleotide types that are simultaneously present can be complementary to at most 4, 3, 2, or 1 nucleotide types in a template nucleic acid.

A method of the present disclosure can include a step of incorporating a nucleotide into a primer. Incorporated nucleotides alternatively can be unlabeled nucleotides, or detectably labeled nucleotide analogs. Whether labeled or not, the nucleotides can be terminator nucleotides that are permanently or reversibly prevented from being extended once incorporated into a primer. The polymerase can dissociate from primed template after nucleotide incorporation.

The incorporation step can be carried out to add a labeled nucleotide. The labeled nucleotide can then be detected, for example, in a sequencing technique. An advantage of extending a nucleic acid with a labeled nucleotide in a method that also detects dissociation of a polymerase from the extended nucleic acid is that combining the results of two different types of molecular characterization can provide added confidence in identifying an allele compared to performing only one of the characterization techniques. Exemplary methods for performing extension assays are set forth in U.S. Pat. No. 6,355,431 or U.S. Pat. No. 9,045,796, each of which is incorporated herein by reference. The methods set forth herein can be used to replace or augment the extension assays set forth in the references.

In particular embodiments, a nucleotide position in a template can be identified without incorporating a labeled nucleotide at the position. For example, an examination step can be carried out where a stabilized ternary complex is formed between a primed template, polymerase and next correct nucleotide. The stabilized ternary complex can be detected to identify the next correct nucleotide. Methods for forming and detecting stabilized ternary complexes are set forth for example in commonly owned US Pat. App. Pub. No. 2017/0022553 A1, which is incorporated herein by reference. Extension can then proceed using non-labelled nucleotides. In further embodiments, a non-labelled nucleotide can be incorporated and identified using a label-free extension detection method such as detection of pyrophosphate release upon polymerase catalyzed incorporation (see, for example, detection methods employed in pyrosequencing techniques) or detection of proton release upon polymerase catalyzed incorporation (see, for example, detection methods employed in Ion Torrent sequencing techniques).

In some embodiments, only a single nucleotide is incorporated at the 3'-end of a primer. For example, the 3' position of the nucleotide can be modified to include a 3' terminator moiety. The 3' terminator moiety may be a reversible terminator or may be an irreversible terminator. Optionally, the reversible terminator nucleotide includes a 3'-ONH$_2$ moiety attached at the 3' position of the sugar moiety. Further examples of useful reversible terminator moieties are described, for example, in Bentley et al., *Nature* 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and U.S. 2008/0108082, each of which is incorporated herein by reference. Optionally, multiple nucleotides are incorporated at the 3'-end of the primer.

For example, the nucleotide that is incorporated can include a 3'-hydroxyl group that is capable of being further extended after incorporation. In some embodiments, the incorporation step is part of a sequencing technique, amplification technique, or other technique for manipulating nucleic acids.

Optionally, a nucleotide that is added to a primer in a method set forth herein can occur as part of a nucleic acid sequencing method. Particularly useful sequencing methods include, but are not limited to, Sequencing By Binding™, Pyrosequencing™, or sequencing by synthesis methods.

Sequencing By Binding™ can be carried out, for example, as described in commonly owned U.S. Pat. App. Pub. No. 2017/0022553 A1, which is incorporated herein by reference. Briefly, methods for determining the sequence of a template nucleic acid molecule can be based on formation of a ternary complex (between polymerase, primed nucleic acid and cognate nucleotide) under specified conditions. The method can generally include an examination step prior to incorporation of a nucleotide. The examination step can involve providing a template nucleic acid molecule primed with a primer; contacting the primed template nucleic acid molecule with a first reaction mixture that includes a polymerase and at least one nucleotide molecule; monitoring the interaction of the polymerase with the primed template nucleic acid molecule in the presence of the nucleotide molecule, without chemical incorporation of the nucleotide molecule into the primed template nucleic acid; and identifying a next base in the template nucleic acid using the monitored interaction of the polymerase with the primed template nucleic acid molecule in the presence of the nucleotide molecule. In this procedure, ternary complex stabilization and binary complex destabilization advantageously enhance discrimination between correct and incorrect nucleotides.

A stabilized ternary complex can be formed by one or a combinations of means, including but not limited to, crosslinking the thumb and finger domains of a polymerase in the closed conformation, binding of an allosteric inhibitor that prevents return of the polymerase to an open conformation, binding of pyrophosphate analogs that trap polymerase in the pre-translocation step, use of a polymerase mutant that is attenuated or inhibited in nucleotidyl transfer activity, or addition of non-catalytic divalent metal ions such as Ca$^{2+}$ and Sr$^{2+}$ as substitutes for a catalytic metal ion. Non-catalytic metal ions include, but are not limited to, calcium, strontium, scandium, titanium, vanadium, chromium, iron, cobalt, nickel, copper, zinc, gallium, germanium, arsenic, selenium, rhodium, europium, and terbium ions. Optionally, conditions that disfavor or destabilize binary complexes (i.e. complexes between polymerase and primed nucleic acid but lacking cognate nucleotide) are provided by the presence of one or more monovalent cations and/or glutamate anions. Another condition that favors or stabilizes a ternary complex includes the presence of a blocking group that precludes enzymatic incorporation of an incoming nucleotide into the primer (e.g. a reversible terminator moiety on the 3' nucleotide of the primer). As a further option, a polymerase engineered to have reduced catalytic activity or reduced propensity for binary complex formation can be used. These and other useful methods for forming stabilized ternary complexes are set forth in commonly owned U.S. Pat. App. Pub. No. 2017/0022553 A1, which is incorporated herein by reference.

Optionally, incorporation of a nucleotide into the primer proceeds after the cognate nucleotide has been identified in an examination procedure. Incorporation optionally may employ a polymerase different from the one used in the examination step, together with a nucleotide. The nucleotide can be the same or different from the nucleotide that was present in the examination step. For example, the nucleotide can be an unlabeled reversible terminator nucleotide corresponding to the identified cognate nucleotide (i.e., the reversible terminator nucleotide and the cognate nucleotide are both complementary to the same base of the template strand).

The incorporation step involves covalently incorporating one or more nucleotides at the 3'-end of a primer hybridized to a template nucleic acid. In a preferred embodiment, only a single nucleotide is incorporated at the 3'-end of the primer. Optionally, multiple nucleotides of the same kind are incorporated at the 3'-end of the primer. Optionally, multiple nucleotides of different kinds are incorporated at the 3'-end of the primer. Incorporated nucleotides alternatively can be unlabeled nucleotides, reversible terminator nucleotides, or detectably labeled nucleotide analogs.

Optionally, the nucleotide enclosed within the ternary complex of the examination step is incorporated into the 3'-end of the template nucleic acid primer during the incorporation step. Optionally, the reaction mixture and/or reaction conditions present during the examination step may be altered to facilitate the incorporation step. These means include, but are not limited to, removing reagents, chelating reagents, diluting reagents, adding reagents, altering reaction conditions such as conductivity or pH, and any combination thereof. Such methods can be used to remove or alter conditions that stabilized ternary complex in a prior examination step.

Alternatively, suitable reaction conditions for incorporation may involve replacing the examination reaction mixture with an incorporation reaction mixture. Optionally, nucleotide(s) present in the examination reaction mixture are replaced with one or more nucleotides in the incorporation reaction mixture. Optionally, the polymerase(s) present during the examination step is replaced during the incorporation step. By this approach it is possible to employ different types of polymerase and/or different types of nucleotides in the examination and incorporation steps.

Accordingly, the present disclosure provides a method for determining the presence of a nucleic acid allele that includes the steps of (a) forming a stabilized ternary complex comprising a polymerase, a double stranded nucleic acid that includes a primer hybridized to a template, and a next correct nucleotide, wherein the template includes a first allele of a locus, and wherein the next correct nucleotide is a cognate to the first allele or to a nucleotide that is adjacent to the first allele in the template; (b) examining the stabilized ternary complex, thereby acquiring a signal for determining the presence of the next correct nucleotide; (c) adding a nucleotide to the primer via a catalytically active polymerase, thereby producing an extended double stranded nucleic acid; (d) dissociating the catalytically active polymerase from the extended double stranded nucleic acid; (e) detecting dissociation of the catalytically active polymerase from the extended double stranded nucleic acid; (f) comparing the dissociation of the catalytically active polymerase from the extended double stranded nucleic acid to dissociation of the catalytically active polymerase from a second double stranded nucleic acid, the second double stranded nucleic acid including a primer hybridized to the same position of the locus as the primer of the extended double stranded nucleic acid; and (g) determining the presence of the first allele in the template nucleic acid based on the signal detected in (b) and based on the comparison in (f).

Also provided is a method for distinguishing nucleic acid alleles by carrying out the steps of (a) providing a first template nucleic acid including a first allele of a locus and a second template nucleic acid including a second allele of the locus, wherein the first and second templates are hybridized to a primer, thereby providing first and second double stranded nucleic acids, respectively; (b) forming a first stabilized ternary complex comprising a polymerase, a double stranded nucleic acid that includes a primer hybridized to the first template, and a first next correct nucleotide, wherein the first next correct nucleotide is a cognate to the first allele or to a nucleotide that is adjacent to the first allele, and forming a second stabilized ternary complex comprising a polymerase, a double stranded nucleic acid that includes a primer hybridized to the second template, and a second next correct nucleotide, wherein the second next correct nucleotide is a cognate to the second allele or to a nucleotide that is adjacent to the second allele; (c) examining the stabilized ternary complexes, thereby acquiring signals for determining the presence of the first and second next correct nucleotides; (d) adding nucleotides to the primers of the first and second double stranded nucleic acids via catalytic activity of the polymerases, thereby producing an extended first double stranded nucleic acid and an extended second double stranded nucleic acid; (e) dissociating the polymerases from the extended double stranded nucleic acids; (f) detecting dissociation of the polymerase from the extended double stranded nucleic acids; and (g) distinguishing the first and second alleles based on the signals detected in (c) and based on the dissociations detected in (f).

Sequencing-by-synthesis (SBS) techniques can also be used. Briefly, SBS can be initiated by contacting a template nucleic acid with one or more nucleotides, DNA polymerase, etc. Primer is extended using the target nucleic acid as template. The primer extension in some embodiments will incorporate a labeled nucleotide that can be detected. Optionally, the nucleotides (whether labeled or not) can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the extended nucleic acid (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use in methods of the present disclosure are described, for example, in Bentley et al., *Nature* 456:53-59 (2008), WO 04/018497; WO 91/06678; WO 07/123744; U.S. Pat. Nos. 7,057,026; 7,329,492; 7,211,414; 7,315,019 or 7,405,281, and U.S. Pat. App. Pub. No. 2008/0108082 A1, each of which is incorporated herein by reference. Also useful are SBS methods that are commercially available from Illumina, Inc., San Diego Calif.

Some SBS embodiments include detection of a proton released upon incorporation of a nucleotide into an extension product. For example, sequencing based on detection of released protons can use an electrical detector and associated techniques that are commercially available from Ion Torrent (a subsidiary of Thermo Fisher, Waltham, MA) or sequencing methods and systems described in U.S. Pat. App. Pub.

Nos. 2009/0026082 A; 2009/0127589 A1; 2010/0137143 A1; or 2010/0282617 A1, each of which is incorporated herein by reference.

Other sequencing procedures can be used, such as Pyrosequencing™. Pyrosequencing™ detects the release of inorganic pyrophosphate (PPi) as particular nucleotides are incorporated into a nascent primer hybridized to a template nucleic acid strand (Ronaghi, et al., *Analytical Biochemistry* 242 (1), 84-9 (1996); Ronaghi, *Genome Res.* 11 (1), 3-11 (2001); Ronaghi et al. *Science* 281 (5375), 363 (1998); U.S. Pat. Nos. 6,210,891; 6,258,568 and 6,274,320, each of which is incorporated herein by reference). In Pyrosequencing™, released PPi can be detected by being converted to adenosine triphosphate (ATP) by ATP sulfurylase, and the resulting ATP can be detected via luciferase-produced photons. Thus, the sequencing reaction can be monitored via a luminescence detection system.

Some embodiments can utilize methods involving the real-time monitoring of DNA polymerase activity. For example, nucleotide incorporations can be detected through fluorescence resonance energy transfer (FRET) interactions between a fluorophore-bearing polymerase and gamma-phosphate-labeled nucleotides, or with zeromode waveguides (ZMW). Techniques and reagents for sequencing via FRET and or ZMW detection are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference.

Accordingly, the present disclosure provides a method for determining the presence of a nucleic acid allele that includes the steps of (a) binding a polymerase to a double stranded nucleic acid that includes a primer hybridized to a template, the template including a first allele of a locus; (b) adding a nucleotide to the primer via catalytic activity of the polymerase, thereby producing an extended double stranded nucleic acid; (c) acquiring a signal for detecting the added nucleotide; (d) dissociating polymerase from the extended double stranded nucleic acid; (e) detecting dissociation of the catalytically active polymerase from the extended double stranded nucleic acid; (f) comparing the dissociation of the polymerase from the extended double stranded nucleic acid to dissociation of the polymerase from a second double stranded nucleic acid, the second double stranded nucleic acid including a primer hybridized to the same position of the locus as the primer of the extended double stranded nucleic acid; and (g) determining the presence of the first allele in the template nucleic acid based on the signal detected in (c) and based on the comparison in (f).

Also provided is a method for distinguishing nucleic acid alleles by carrying out the steps of (a) providing a first template nucleic acid including a first allele of a locus and a second template nucleic acid including a second allele of the locus, wherein the first and second templates are hybridized to a primer, thereby providing first and second double stranded nucleic acids, respectively; (b) binding polymerases to the first and second double stranded nucleic acids; (c) adding nucleotides to the primers of the first and second double stranded nucleic acids via catalytic activity of the polymerases, thereby producing an extended first double stranded nucleic acid and an extended second double stranded nucleic acid; (d) acquiring signals for detecting the added nucleotides; (e) dissociating polymerases from the extended double stranded nucleic acids; (f) detecting dissociation of the polymerase from the extended double stranded nucleic acids; and (g) distinguishing the first and second alleles based on the signals detected in (d) and based on the dissociations detected in (f).

A method of the present disclosure can include a step of detecting the rate at which a complex between a polymerase and extended nucleic acid dissociates. Generally, detection can be achieved by methods that perceive properties that are intrinsic to a component of a polymerase-nucleic acid complex or properties of label moieties on one or more component of the complex. Exemplary properties upon which detection can be based include, but are not limited to, mass, electrical conductivity, energy absorbance, fluorescence or the like. Detection of fluorescence can be carried out using methods known in the art pertaining to nucleic acid arrays. A fluorophore can be detected based on any of a variety of fluorescence phenomena including, for example, emission wavelength, excitation wavelength, fluorescence resonance energy transfer (FRET) intensity, quenching, anisotropy or lifetime. Other detection techniques that can be used in a method set forth herein include, for example, mass spectrometry which can be used to perceive dissociation due to reduction in mass; surface plasmon resonance which can be used to perceive dissociation from a surface; absorbance which can be used to perceive dissociation based on loss of signal due to dissociation of a complex; calorimetry which can be used to perceive changes in temperature due dissociation of a complex; electrical conductance or impedance which can be used to perceive a loss of electrical properties due to dissociation of a complex, or other known analytic techniques. Further techniques for detecting biological components or label moieties are set forth, for example, in commonly owned U.S. Pat. App. Pub. No. 2017/0022553 A1 or in U.S. Pat. No. 6,355,431 or U.S. Pat. No. 9,045,796, each of which is incorporated herein by reference.

A polymerase-nucleic acid complex that is made or used in accordance with the present disclosure may optionally include one or more exogenous label(s). The label can be present on the polymerase, template nucleic acid and/or primer. For example, the label can be present on a nucleotide that has been added to the 3' end of the primer, for example, due to activity of the polymerase in the complex or due to the activity of a polymerase that previously interacted with the primer. In the case of a ternary complex between polymerase, nucleic acid and cognate nucleotide, the label can be present on the polymerase, template nucleic acid, primer and/or cognate nucleotide.

Further examples of useful exogenous labels include, but are not limited to, radiolabel moieties, fluorophore moieties, quantum dot moieties, chromophore moieties, enzyme moieties, electromagnetic spin labeled moieties, nanoparticle light scattering moieties, and any of a variety of other signal generating moieties known in the art. Exemplary fluorophore moieties include, but are not limited to umbelliferone, fluorescein, isothiocyanate, rhodamine, tetramethyl rhodamine, eosin, green fluorescent protein, erythrosin, coumarin, methyl coumarin, pyrene, malachite green, stilbene, lucifer yellow™, Cascade Blue™, Texas Red™, dansyl chloride, phycoerythrin, phycocyanin, fluorescent lanthanide complexes such as those including Europium and Terbium, Cy3, Cy5, and others known in the art as described, for example, in *Principles of Fluorescence Spectroscopy*, Joseph R. Lakowicz (Editor), Plenum Pub Corp, 2nd edition (July 1999) and the 6th Edition of *Molecular Probes Handbook* by Richard P. Hoagland.

In alternative embodiments, one or more components of a polymerase-nucleic acid complex can lack exogenous labels. For example, a ternary complex and components used in the formation of the ternary complex (e.g. polymerase, template nucleic acid, primer and/or cognate nucleotide) can lack one, several or all of the exogenous labels described herein or in the references incorporated herein. In such embodiments, ternary complexes can be detected based on intrinsic properties of the stabilized ternary complex, such as mass, charge, intrinsic optical properties or the like. Exemplary methods for detecting non-labeled ternary complexes are set forth in commonly owned U.S. Pat. App. Pub. No. 2017/0022553 A1, which is incorporated herein by reference.

In some embodiments, one or more of the steps for the methods presented herein can be repeated. Repetitive cycles of detecting extension products followed by detecting dissociation rates can be used to obtain a more accurate characterization of a nucleic acid sequence than would be available absent the dissociation rate measurements. Repetition is particularly useful for embodiments where primer extension is carried out as part of a sequencing method. More specifically, each repetition can include detection of the nucleotide that is added by extension and detection of the rate at which polymerase dissociates from the extension product. As exemplified by these sequencing embodiments, a method set forth herein can be repeated one or more times to produce and detect a serially extended primer hybridized to a template. The number of repetitions can be performed to obtain serial extensions of at least 2, 3, 4, 5, 10, 25, 50, 100 or more nucleotides. Alternatively or additionally, the number of repetitions can be limited to obtain serial extensions of at most 100, 50, 25, 10, 5, 4, 3 or 2 nucleotides.

Accordingly, the present disclosure provides a method for determining the presence of a nucleic acid allele that includes steps of (a) binding a polymerase to a double stranded nucleic acid that includes a primer hybridized to a template, the template including a first allele of a locus; (b) adding a nucleotide to the primer via catalytic activity of the polymerase, thereby producing an extended double stranded nucleic acid; (c) dissociating the polymerase from the extended double stranded nucleic acid; (d) detecting dissociation of the polymerase from the extended double stranded nucleic acid; (e) comparing the dissociation of the polymerase from the extended double stranded nucleic acid to dissociation of the polymerase from a second double stranded nucleic acid, the second double stranded nucleic acid including a primer hybridized to the same position of the locus as the primer of the extended double stranded nucleic acid, thereby determining the presence of the first allele in the template nucleic acid; and repeating steps (a) through (e) using the extended double stranded nucleic acid in place of the double stranded nucleic acid, whereby a serially extended double stranded nucleic acid is produced.

Also provided is a method for determining the presence of a nucleic acid allele that includes the steps of (a) binding a polymerase to a double stranded nucleic acid that includes a primer hybridized to a template, the template including a first allele of a locus; (b) adding a nucleotide to the primer via catalytic activity of the polymerase, thereby producing an extended double stranded nucleic acid; (c) dissociating the polymerase from the extended double stranded nucleic acid; (d) detecting the dissociation of the polymerase from the extended double stranded nucleic acid; (e) comparing the dissociation of the polymerase from the extended double stranded nucleic acid to dissociation of the polymerase from a second double stranded nucleic acid, the second double stranded nucleic acid including a primer hybridized to the same position of the locus as the primer of the extended double stranded nucleic acid, thereby determining the presence of the first allele in the template nucleic acid; (f) binding a polymerase to the extended double stranded nucleic acid; (g) adding a nucleotide to the primer of the extended double stranded nucleic acid via catalytic activity of the polymerase, thereby producing a serially extended double stranded nucleic acid; (h) dissociating the polymerase from the serially extended double stranded nucleic acid; (i) detecting the dissociation of the polymerase from the serially extended double stranded nucleic acid; and (j) comparing the dissociation of the polymerase from the serially extended double stranded nucleic acid to dissociation of the polymerase from a third double stranded nucleic acid, the third double stranded nucleic acid including a primer hybridized to the same positions of the locus as the primer of the serially extended double stranded nucleic acid.

In a further embodiment, a method for distinguishing nucleic acid alleles can include steps of (a) providing a first template nucleic acid including a first allele of a locus and a second template nucleic acid including a second allele of the locus, wherein the first and second templates are hybridized to a primer, thereby providing first and second double stranded nucleic acids, respectively; (b) binding polymerases to the first and second double stranded nucleic acids; (c) adding nucleotides to the primers of the first and second double stranded nucleic acids via catalytic activity of the polymerases, thereby producing an extended first double stranded nucleic acid and an extended second double stranded nucleic acid; (d) dissociating the polymerases from the extended double stranded nucleic acids; (e) detecting the dissociation of the polymerase from the extended double stranded nucleic acids; (f) determining a difference in the dissociation of the polymerase from the first extended double stranded nucleic acid to the dissociation of the polymerase from the second extended double stranded nucleic acid, thereby distinguishing the first allele from the second allele; (g) binding a polymerases to the extended first double stranded nucleic acid and the extended second double stranded nucleic acid; (h) adding nucleotides to the primers of the extended first and second double stranded nucleic acids via catalytic activity of the polymerases, thereby producing serially extended first and second double stranded nucleic acids; (i) dissociating the polymerases from the serially extended first and second double stranded nucleic acids; (j) detecting the dissociation of the polymerase from the serially extended first and second double stranded nucleic acids; and (k) determining a difference in the dissociation of the polymerase from the first serially extended double stranded nucleic acid to the dissociation of the polymerase from the second serially extended double stranded nucleic acid, thereby distinguishing the first allele from the second allele.

A method of the present disclosure can be repeated to extend a primer through one or more of a region that is downstream of an allele, a region where the allele occurs and a region that is upstream of the allele. For example, a primer can be extended by adding one or more nucleotides that are downstream of a SNP allele and then adding a cognate of the SNP to the primer. Alternatively, a primer can be extended by adding a cognate of a SNP allele to the primer and then by adding one or more nucleotides that are upstream of the SNP. As a third example, a primer can be extended by adding one or more nucleotides that are downstream of a SNP allele, then adding a cognate of the SNP to the primer, and then adding one or more nucleotides that are upstream of the SNP. In all three examples, dissociation rates can be detected after one or more of the nucleotide additions. The alleles can be distinguished based on a comparison of polymerase-nucleic acid dissociation rates for test nucleic acid to the dissociation rates for control nucleic acids.

In particular embodiments, a nucleotide that is added to a primer is a cognate to an allelic position of the template to which the primer is hybridized. A nucleotide can then be added to the extended primer, the nucleotide being a cognate to a position of the template that is adjacent to the allelic position. In other embodiments, a nucleotide that is added to a primer is a cognate to a position of the template (to which the primer is hybridized) that is adjacent to an allelic position, and then a nucleotide that is a cognate to the allelic position can be added to the extended primer.

Embodiments of the methods set forth herein can be particularly advantageous for distinguishing variants in a nucleic acid template that are difficult to distinguish due to being located in, or adjacent to, a homopolymer region that is sequenced under homopolymer compression conditions. Often it is difficult to accurately identify the number of nucleotides that were added in a homopolymer region due to limitations in the dynamic range for signal acquisition or due to non-linearity between signal intensity and number of nucleotides incorporated. The comparative dissociation methods set forth herein can be employed to distinguish a sequence variant at or near a homopolymer based on the effect the different sequences have on polymerase dissociation rate.

Accordingly, a locus that is detected in a method set forth herein can include a homopolymer region and an allele that is detected can be located at a position that is in the homopolymer region or adjacent to the homopolymer region. A plurality of nucleotides of one type can be added to a primer that is hybridized to the homopolymer region, thereby producing an extended primer that is complementary to the homopolymer region. The nucleotides may have extendible 3' hydroxyl moieties such that the length of the extension to the primer is determined by the length of the homopolymer (this contrasts with methods that add only one nucleotide per cycle due to presence of a reversible blocking moiety on the nucleotide). After extension through the homopolymer is complete, the polymerase can be dissociated from the nucleic acid and the rate at which it dissociates can be compared to the dissociation rate of a polymerase bound to a control nucleic acid.

A polymerase-nucleic acid complex, or a component that is capable of forming (i.e. participating in the formation of) such a complex, can be attached to a solid support. The solid support can be made from any of a variety of materials set forth herein. Suitable materials may include glass, polymeric materials, silicon, quartz (fused silica), borofloat glass, silica, silica-based materials, carbon, metals, an optical fiber or bundle of optical fibers, sapphire, or plastic materials. The particular material can be selected based on properties desired for a particular use. For example, materials that are transparent to a desired wavelength of radiation are useful for analytical techniques that will utilize radiation of that wavelength. Conversely, it may be desirable to select a material that does not pass radiation of a certain wavelength (e.g. being opaque, absorptive or reflective). Other properties of a material that can be exploited are inertness or reactivity to certain reagents used in a downstream process, such as those set forth herein; or ease of manipulation or low cost of manufacture.

A particularly useful solid support is a particle such as a bead or microsphere. Populations of beads can be used for attachment of populations of polymerase-nucleic acid complexes or components capable of forming the complexes (e.g. polymerases, templates, primers or nucleotides). In some embodiments, it may be useful to use a configuration whereby each bead has a single type of polymerase-nucleic acid complex or a single type of component capable of forming the complex. For example, an individual bead can be attached to a single type of polymerase-nucleic acid complex, a single type of template allele, a single type of allele-specific primer, a single type of locus-specific primer or a single type of nucleotide. Alternatively, different types of components need not be separated on a bead-by-bead basis. As such, a single bead can bear multiple different types of polymerase-nucleic acid complexes, template alleles, allele-specific primers, locus-specific primers and/or nucleotides. The composition of a bead can vary, depending for example, on the format, chemistry and/or method of attachment to be used. Exemplary bead compositions include solid supports, and chemical functionalities imparted thereto, used in protein and nucleic acid capture methods. Such compositions include, for example, plastics, ceramics, glass, polystyrene, melamine, methylstyrene, acrylic polymers, paramagnetic materials, thoria sol, carbon graphite, titanium dioxide, latex or cross-linked dextrans such as Sepharose™, cellulose, nylon, cross-linked micelles and Teflon™, as well as other materials set forth in "Microsphere Detection Guide" from Bangs Laboratories, Fishers Ind., which is incorporated herein by reference.

The geometry of a particle, bead or microsphere also can correspond to a wide variety of different forms and shapes. For example, they can be symmetrically shaped (e.g. spherical or cylindrical) or irregularly shaped (e.g. controlled pore glass). In addition, beads can be porous, thus increasing the surface area available for capture of ternary complexes or components thereof. Exemplary sizes for beads used herein can range from nanometers to millimeters or from about 10 nm-1 mm.

In particular embodiments, beads can be arrayed or otherwise spatially distinguished. Exemplary bead-based arrays that can be used include, without limitation, a BeadChip' Array available from Illumina, Inc. (San Diego, CA) or arrays such as those described in U.S. Pat. Nos. 6,266,459; 6,355,431; 6,770,441; 6,859,570; or 7,622,294; or PCT Publication No. WO 00/63437, each of which is incorporated herein by reference. Beads can be located at discrete locations, such as wells, on a solid-phase support, whereby each location accommodates a single bead. Alternatively, discrete locations where beads reside can each include a plurality of beads as described, for example, in U.S. Pat. App. Pub. Nos. 2004/0263923 A1, 2004/0233485 A1, 2004/0132205 A1, or 2004/0125424 A1, each of which is incorporated herein by reference.

As will be recognized from the above bead array embodiments, a method of the present disclosure can be carried out in a multiplex format whereby multiple different types of nucleic acids are detected in parallel in a method set forth herein. Although it is also possible to serially process different types of nucleic acids using one or more steps of the methods set forth herein, parallel processing can provide cost savings, time savings and uniformity of conditions.

Further examples of commercially available arrays that can be used include, for example, an Affymetrix GeneChip™ array. A spotted array can also be used according to some embodiments. An exemplary spotted array is a CodeLink™ Array available from Amersham Biosciences. Another array that is useful is one that is manufactured using inkjet printing methods such as SurePrint™ Technology available from Agilent Technologies.

Nucleic acid arrays can be configured such that the nucleic acids that are attached at the features have a 3' end that is accessible to interaction with a polymerase. In such embodiments, the 3' end of the attached primer can participate in ternary complex formation, polymerase catalyzed extension or polymerase dissociation. For example, primers can be attached to features via the 5' end of the primer or at another portion of the primer that does not sterically block interaction of the 3' end with a polymerase.

Other useful arrays include those that are used in nucleic acid sequencing applications. For example, arrays that are used to attach amplicons of genomic fragments (often referred to as clusters) can be particularly useful. Examples of nucleic acid sequencing arrays that can be modified for use herein include those described in Bentley et al., *Nature* 456:53-59 (2008), PCT Pub. Nos. WO 91/06678; WO 04/018497 or WO 07/123744; U.S. Pat. Nos. 7,057,026; 7,211,414; 7,315,019; 7,329,492 or 7,405,281; or U.S. Pat. App. Pub. No. 2008/0108082, each of which is incorporated herein by reference.

As set forth above, embodiments of the methods that employ attached nucleic acids can use arrays that are known in the art and in some cases arrays that are commercially available. Moreover, linkages made from commercial arrays (or other nucleic acid arrays) to nucleic acid probes can be replaced with linkages for attaching polymerases or nucleotides to surfaces. In other embodiments, templates, primers, polymerases or nucleotides can be attached to oligonucleotide moieties that are complementary to probes located on nucleic acid arrays. In such embodiments, the template, primer, nucleotide or polymerase can be attached to the surface via hybridization or crosslinking of the complementary strands.

A polymerase-nucleic acid complex or component that is used to make such a complex can be attached to an array or other solid support using any of a variety of methods well known in the art. Such methods include, for example, attachment by direct chemical synthesis onto the solid support, chemical attachment, photochemical attachment, thermal attachment, enzymatic attachment and/or absorption. These and other methods are well known in the art and applicable for attachment of proteins, nucleotides or nucleic acids in any of a variety of formats and configurations. Attachment to a solid support can occur via a covalent linkage or via non-covalent interactions. Exemplary non-covalent interactions are those between a ligand-receptor pair such as streptavidin (or analogs thereof) and biotin (or analogs thereof) or between an antibody (or functional fragment thereof such as a Fab or ScFv) and epitope. Other useful receptor-ligand pairs include lectin and carbohydrate, and complementary first and second strands of a double-stranded nucleic acid.

Other chemistry conditions and linkages that are useful are those known as "click chemistry" (e.g. U.S. Pat. Nos. 6,737,236; 7,427,678, each incorporated herein by reference in its entirety). Also useful are azide alkyne Huisgen cycloaddition reactions, which use a copper catalyst (e.g. U.S. Pat. Nos. 7,375,234; 7,763,736, each incorporated herein by reference in its entirety). Copper-free Huisgen reactions ("metal-free click") using strained alkynes can be employed. Other useful linkage chemistries include, but are not limited to triazine-hydrazine moieties which can link to aldehyde moieties, for example, as described in U.S. Pat. No. 7,259, 258, which is incorporated by reference; triazine chloride moieties which can link to amine moieties; carboxylic acid moieties which can link to amine moieties using a coupling reagent, such as EDC; thiol moieties which can link to thiol moieties; alkene moieties which can link to dialkene moieties that are coupled through Diels-Alder reactions; and acetyl bromide moieties which can link to thiophosphate moieties, such as those described in WO 2005/065814, which is incorporated by reference. Glass-like surfaces can also be modified with various glass-reactive molecules, such as functionalized silanes, some of which are commercially available from Gelest, Inc.

In particular embodiments, a polymerase-nucleic acid complex, polymerase, nucleic acid or nucleotide is attached to a flow cell surface or to a solid support in a flow cell. A flow cell allows convenient fluidic manipulation by passing solutions into and out of a fluidic chamber that contacts the support-bound, complex. The flow cell also provides for detection of the fluidically manipulated components. For example, a detector can be positioned to detect signals from the solid support, such as signals from a label that disappears from the solid support due to dissociation of a polymerase-nucleic acid complex. Exemplary flow cells that can be used are described, for example, in U.S. Pat. App. Publ. No. 2010/0111768 A1, WO 05/065814 and U.S. Pat. App. Publ. No. 2012/0270305 A1, each of which is incorporated herein by reference.

Optionally, the provided methods further include a wash step. The wash step can occur before or after any other step in the method. For example, a method set forth herein can optionally include a step of washing a solid support after forming one or more polymerase-nucleic acid complexes or after a step of a sequencing technique. The wash can provide the advantage of removing contaminants such as components of a mixture from which one or more components of the stabilized ternary complex were derived. In particular embodiments, the wash step occurs under conditions that stabilize a polymerase-nucleic acid complex. For example, a wash step can employ one or more of the stabilizing conditions or stabilizing agents set forth herein or in commonly owned U.S. Pat. App. Pub. No. 2017/0022553 A1, which is incorporated herein by reference. Optionally, the wash solution includes nucleotide(s) of the same type as the next correct nucleotide(s) used during formation of a stabilized ternary complex. Including the next correct nucleotide(s) at a sufficient concentration can provide the advantage of stabilizing previously formed ternary complexes from unwanted disassociation.

Example I

Examination of a Series of Primed Template
Nucleic Acid Molecules

This example demonstrates that polymerase dissociation measurements have sequence specific features that can be used to distinguish sequence variants.

A FORTEBIO® (Menlo Park, CA) Octet instrument employing biolayer interferometry to measure binding reactions at the surface of a fiber optic tip was used in a multiwell plate format to illustrate the sequencing technique. The reagent plate was maintained at 37° C. for the duration of the experiment. Template strands biotinylated at their 5'-ends were hybridized to primers and immobilized onto fiber optic tips functionalized with streptavidin (SA). Upon DNA primer-template hybridization, the fiber optic tips were equilibrated in Al buffer composed of 30 mM Tris (pH 8.0), 220 mM KCl, 160 mM potassium glutamate, 0.01% Tween-20, and 0.1 mg/ml ultrapure bovine serum albumin.

Sequencing By Binding™ (SBB™) methodology was then carried out as follows. In a binding step, the equilibrated fiber optic tips were contacted, for a duration of 20 seconds, with one of four native dNTP nucleotides (0.1 mM dATP, 0.1 mM dGTP, 0.1 mM dCTP, or 0.3 mM dTTP) and 120 units/mL of Bst DNA polymerase (New England Bio-Labs Inc.; Ipswich, MA) in the A1 buffer additionally containing 3% DMSO, 0.3 M betaine, 1 mM β-mercapto-ethanol, and 5 mM strontium chloride. During the binding step, optical interferometry measurements were recorded at regular intervals by the Octet instrument. The binding step was followed by an incorporation/dissociation step in which the fiber optic tips were dunked into the incorporation solution (A1 buffer additionally containing 3% DMSO, 0.3 M betaine, 1 mM β-mercaptoethanol, and 2 mM magnesium chloride) and further interferometry measurements were recorded by the Octet instrument. After the incorporation/dissociation step, biosensors were washed with a solution that included 20 mM EDTA for 25 seconds to chelate magnesium ions. The biosensors were then equilibrated with regeneration buffer that included 30 mM Tris (pH 8.0), 220 mM KCl, 160 mM potassium glutamate, 1 mM MgCl$_2$, 0.01% Tween-20, 1 mM β-mercaptoethanol. Each sequenc-ing cycle included the above binding, incorporation/disso-ciation, wash and detection steps. Thirty cycles were carried out, serially presenting the four different nucleotides (in order A, T, G, C, A, T, G, C, etc.) until collecting binding and dissociation curves for all four dNTPs.

The sequences for three templates and the primer used in the experiments are shown in Table 1. The PhiX_FP2-long-biot oligo was used as a primer hybridized to the three templates: phiX-wt, phiX-m2 and phiX-m3. Primer binding regions in the template oligos are underlined. SNPs in the phiX-m2 and phiZ-m3 templates that differ from the wt template are highlighted in bold.

TABLE 1

| Sequences of the nucleic acids used in the experiment | |
| --- | --- |
| phiX-wt | AGAAGGCGGTTCCTGAATGAATGGGAAGCCTTCAAGAAGG TGATAAGCAGGAGAAACATAC<u>GAAGGCGCATAACGATACC ACTGACCCTC</u> (SEQ ID NO: 1) |
| phiX-m2 | AGAAGGCGGTTCCTGAATGAATGGGAAGCCTTCAAGAAGG TGATAAGCAGGAGGAACATAC<u>GAAGGCGCATAACGATACC ACTGACCCTC</u> (SEQ ID NO: 2) |
| phiX-m3 | AGAAGGCGGTTCCTGAATGAATGGGAAGCCTTCAAGAAGG TGATAAGCAGAAGAAACATAC<u>GAAGGCGCATAACGATACC ACTGACCCTC</u> (SEQ ID NO: 3) |
| PhiX_FP2-long-biot | /5Biosg/-GAAGGCGCATAACGATACCACTGACCCTC (SEQ ID NO: 4) |

Time-series interferometry measurements of polymerase dissociation were observed to produce sequence specific results. Specifically, the variation between time-series data of different template nucleotide sequences was significantly greater than the variation of the time-series data of identical nucleotide sequences. This was shown by parameterizing the time-series curves and showing that the distributions of parameter values for different sequences did not overlap.

Examples of time-series parameterizations that can be used to distinguish sequences include (a) fitting an exponential curve to the data and using the exponential amplitude and rate for classification (either or both parameters can be used for classification of sequence information), or (b) observing the initial rate of change of the data (see below).

Figure 1A:
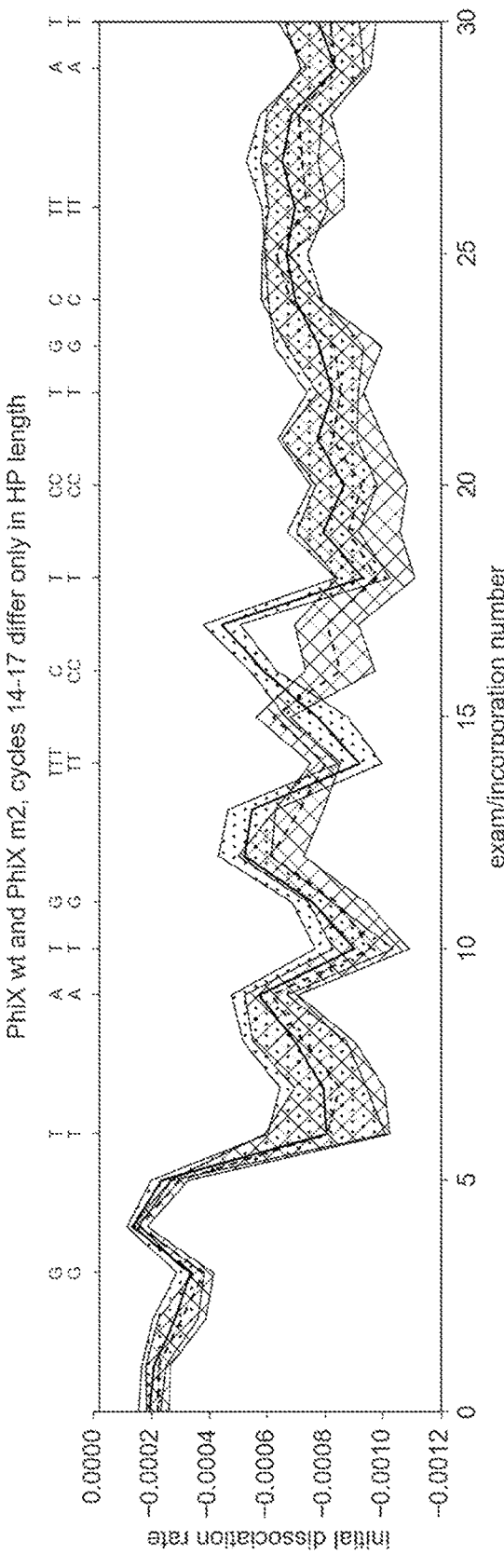
Figure 1B:
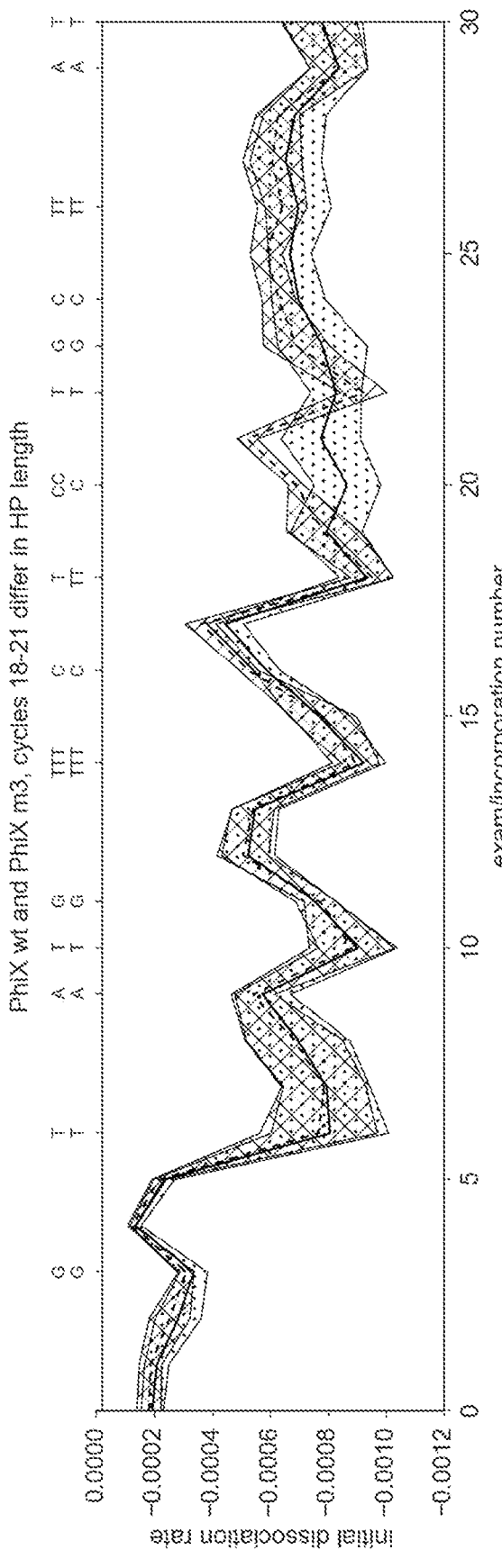
FIG. 1B is a graph showing a plot of initial dissociation rates measured during incorporation/dissociation steps for each cycle of a Sequencing By Binding' run performed with a PhiX wild type template and the PhiX m3 mutant.

FIG. 1A and FIG. 1B show comparisons of initial rate of change on incorporation/dissociation steps for each incor-poration attempt for wild-type and two point mutations, respectively (all sequences found in Table 1). Each sequence was examined 3 times and at each incorporation number the initial rate of change at the dissociation/incorporation step was measured. The mean (line) and the standard deviation (symmetric fill around line) are plotted for each sample as a function of incorporation number. Incorporation number is a count of cycles performed, independent of whether primer extension actually occurs. Actual incorporation of nucleo-tide(s) at a given cycle is indicated by A, C, T or G above the plots in FIG. 1. Most cycles do not result in an actual incorporation (e.g. the first two cycles in the figures do not result in any nucleotides incorporated whereas the third cycle results in incorporation of a G nucleotide). As is also demonstrated by the figure, incorporations at a homopoly-mer will incorporate the full length of the homopolymer (e.g. cycle 14 resulted in three T nucleotides being incor-porated at the adenine trimer of phiX-wt, whereas only two T nucleotides incorporate at the adenine dimer of phiX-m2). The distributions of the rates have statistically significant differences depending on incorporation number.

In the m2 mutant the wild-type sequence GTTTCT is mutated to GTTCCT. As shown in FIG. 1A, statistically significant changes are observed in the initial rate estimation ranging from cycles 12-17 in correspondence with the position of the point mutation. While classification can be accurately done using the initial-rate on cycle number 17 alone, combining cycles 12-17 and combining multiple parameters from the curve parameterization gives additional statistical power. In the m3 mutant similar departures are observed in FIG. 1B where the CTCCTG sequence in the wildtype was mutated to CTTCTG.

The amplitude of signals detected during examination steps of a Sequencing By Binding™ run can be used to determine sequence information, for example, as set forth in commonly owned U.S. Pat. App. Pub. No. 2017/0022553 A, which is incorporated herein by reference. The results of this Example demonstrate that the rate of signal decay observed during incorporation steps of a Sequencing By Binding™ run can be used extract sequencing information. Accord-ingly, the signal amplitude information can be used to identify the next correct nucleotide, while the decay infor-mation can be used to distinguish two different sequences, such as homopolymer repeats of different length.

Throughout this application various publications, patents and/or patent applications have been referenced. The dis-closures of these documents in their entireties are hereby incorporated by reference in this application.

A number of embodiments have been described. Never-theless, it will be understood that various modifications may be made. Accordingly, other embodiments are within the scope of the following claims.

What is claimed is:

1. A method for determining the presence of an allele, comprising (a) binding a polymerase to a double stranded nucleic acid that comprises an extendible primer hybridized to a template;

(b) adding a plurality of nucleotides to the extendable primer via catalytic activity of the polymerase, thereby producing an extended primer that is complementary to a homopolymer region of the allele;

(c) dissociating the polymerase from the extended double stranded nucleic acid; and (d) detecting dissociation of the polymerase from the extended double stranded nucleic acid;

(e) comparing the dissociation of the polymerase from the extended double stranded nucleic acid to dissociation of the polymerase from a second extended double stranded nucleic acid, thereby determining the allele at or near the homopolymer region, wherein the allele is identified based on the comparing of the dissociations in step (e);

wherein step (b) comprises a step in a sequencing method; and wherein the polymerase comprises an exogenous label.

* * * * *